(12) United States Patent
Gu et al.

(10) Patent No.: US 11,680,100 B2
(45) Date of Patent: Jun. 20, 2023

(54) B7-H3 ANTIBODY, ANTIGEN-BINDING FRAGMENT THEREOF AND MEDICAL USE THEREOF

(71) Applicants: Hansoh (Shanghai) Healthtech Co., Ltd., Shanghai (CN); Changzhou Hansoh Pharmaceutical Co., Ltd., Shanghai (CN)

(72) Inventors: Jinming Gu, Shanghai (CN); Xiaohua Wang, Shanghai (CN); Xin Ye, Shanghai (CN); Liuqing Yang, Shanghai (CN); Ting Zhang, Shanghai (CN); Weikang Tao, Shanghai (CN); Lianshan Zhang, Shanghai (CN)

(73) Assignees: Hansoh (Shanghai) Healthtech Co., Ltd., Shanghai (CN); Changzhou Hansoh Pharmaceutical Co., Ltd., Changzhou (CN)

( * ) Notice: Subject to any disclaimer, the term of this patent is extended or adjusted under 35 U.S.C. 154(b) by 106 days.

(21) Appl. No.: 17/121,893

(22) Filed: Dec. 15, 2020

(65) Prior Publication Data

US 2021/0101984 A1    Apr. 8, 2021

Related U.S. Application Data

(63) Continuation of application No. 16/497,687, filed as application No. PCT/CN2018/081249 on Mar. 30, 2018, now Pat. No. 10,899,837.

(30) Foreign Application Priority Data

Mar. 31, 2017 (CN) .......................... 201710206261.2

(51) Int. Cl.
*A61K 39/395* (2006.01)
*A61K 39/00* (2006.01)
*C07K 16/28* (2006.01)
*G01N 33/577* (2006.01)

(52) U.S. Cl.
CPC ....... *C07K 16/2827* (2013.01); *G01N 33/577* (2013.01); *C07K 2317/21* (2013.01); *C07K 2317/92* (2013.01); *G01N 2333/70532* (2013.01)

(58) Field of Classification Search
None
See application file for complete search history.

(56) References Cited

U.S. PATENT DOCUMENTS

| 9,371,395 B2 | 6/2016 | Takahashi et al. |
| 10,316,093 B2 | 6/2019 | Cheung et al. |
| 10,683,364 B2 | 6/2020 | Johnson et al. |
| 2020/0031934 A1 | 1/2020 | Gu et al. |

FOREIGN PATENT DOCUMENTS

| CN | 101104639 B | 1/2008 |
| CN | 102892426 B | 8/2016 |
| CN | 103687945 B | 10/2016 |
| CN | 106279416 A | 1/2017 |
| WO | 2008066691 A2 | 6/2008 |
| WO | 2008100934 A1 | 8/2008 |
| WO | 2010096734 A2 | 8/2010 |
| WO | 2011109400 A2 | 9/2011 |
| WO | 2012147713 A1 | 11/2012 |
| WO | 2015181267 A1 | 12/2015 |
| WO | 2016044383 A1 | 3/2016 |

OTHER PUBLICATIONS

Picarda et al. Molecular Pathways: Targeting B7-H3 (CD276) for Human Cancer Immunotherapy. Clin Cancer Res. Jul. 15, 2016; 22(14): 3425-3431. (Year: 2016).*
Zhou et al., "4IgB7-H3 is the major isoform expressed on immunocytes as well as malignant cells," Tissue Antigens, vol. 70, No. 2, pp. 96-104, Aug. 2007.
Zhang et al., "Diagnosis value of serum B7-H3 expression in non-small cell lung cancer," Lung Cancer, vol. 66, No. 2, pp. 245-246, Nov. 2009.
Crispen et al., "Tumor Cell and Tumor Vasculature Expression of B7-H3 Predict Survival in Clear Cell Renal Cell Carcinoma," Clinical Cancer Research, vol. 14, No. 16, pp. 5150-5157, Aug. 2008.
Roth et al., "B7-H3 Ligand Expression by Prostate Cancer: A Novel Marker of Prognosis and Potential Target for Therapy," Cancer Research, vol. 67, No. 16, pp. 7893-7900, Aug. 2007.
Zang et al., "Tumor associated endothelial expression of B7-H3 predicts survival in ovarian carcinomas," Modern Pathology, vol. 23, No. 8, pp. 1104-1112, Aug. 2010.
Kopp et al., "Targeted immunotherapy for pediatric solid tumors," Journal of OncoImmunology, vol. 97, No. 3, pp. 409-418, 2010.
Kretzschmar et al., "Antibody discovery: phage display," Current Opinion in Biotechnology, vol. 13, pp. 598-602, Dec. 2002.
Pellerin et al., "Defects of filaggrin-like proteins in both lesional and nonlesional atopic skin," Immunotechnology, vol. 48, No. 13, pp. 63-73, 2013.
Holliger et al., "'Diabodies': Small bivalent and bispecific antibody fragments," Proceedings of the National Academy of Sciences of the United States of America, vol. 90, pp. 6444-6448, Jul. 1993.
Alfthan et al., "Properties of a single-chain antibody containing different linker peptides," Protein Engineering, vol. 8, No. 7, pp. 725-731, 1995.

(Continued)

*Primary Examiner* — Maher M Haddad
(74) *Attorney, Agent, or Firm* — Ice Miller LLP

(57) ABSTRACT

A B7-H3 antibody, an antigen-binding fragment thereof and a medical use thereof are provided. Furthermore, a pharmaceutical composition containing the B7-H3 antibody or antigen-binding fragment thereof, and the use thereof as a medicament are provided. In particular, a use of a human B7-H3 antibody or antigen-binding fragment thereof for the manufacture of a medicament for the treatment of a B7-H3-associated disease or condition are described.

17 Claims, 2 Drawing Sheets
Specification includes a Sequence Listing.

(56) References Cited

OTHER PUBLICATIONS

Choi et al., "Recombinant chimeric OKT3 scFv IgM antibodies mediate immune suppression while reducing T cell activation in vitro," European Journal of Immunology, vol. 31, pp. 94-106, 2001.

Hu et al., "Minibody: A Novel Engineered Anti-Carcinoembryonic Antigen Antibody Fragment (Single-Chain Fv-CH3) Which Exhibits Rapid, High-Level Targeting of Xenografts," Cancer Research, vol. 56, pp. 3055-3061, Jul. 1996.

Kipriyanov et al., "Bispecific Tandem Diabody for Tumor Therapy with Improved Antigen Binding and Pharmacokinetics," Journal of Molecular Biology, vol. 293, pp. 41-56, 1999.

Todorovska et al., "Design and application of diabodies, triabodies and tetrabodies for cancer targeting," Journal of Immunological Methods, vol. 248, pp. 47-66, 2001.

International Search Report dated Jun. 21, 2018, for International Patent Application No. PCT/CN2018/081249.

Feng et al., "Isolation of rabbit single domain antibodies to B7-H3 via protein immunization and phage display." Antibody Therapeutics, 2020, vol. 3, No. 1 10-17 (Year:2020).

Loo, Deryk, et al. "Development of an Fc-Enhanced Anti-B7-H3 Monoclonal Antibody with Potent Antitumor Activity," Clinical Cancer Research, Jul. 15, 2021, vol. 18, No. 14, pp. 3834-3845.

Extended European Search Report for European Patent Application No. 18776535.9, issued by the European Patent Office, including Communication, 3 pages Form 1703, Information on Search Strategy, Supplementary European Search Report, and 2-pages Annex, 8 pages.

Huang, Chenglin al. "B7-H3, B7-H4, Foxp3 and IL-2 expression in cervical cancer: Associations with patient outcome and clinical significance," Oncology Reports, vol. 35 (2016) pp. 2183-2190.

Wang, Ling et al. "Roles of coinhibitory molecules B7-H3 and B7-H4 in esophageal squamous cell carcinoma," Tumor Biology, vol. 37 (Sep. 28, 2015) pp. 2961-2971.

Benzon, B. et al. "Correlation of B7-H3 with androgen receptor, immune pathways and poor outcome in prostate cancer: an expression based analysis," Prostate Cancer and Prostatic Diseases, vol. 20 (Nov. 1, 2016) pp. 1-8.

Flem-Karlesn, Karine et al. "Immunoregulatory Protein B7-H3 Promotes Growth and Decreases Sensitivity to Therapy in Metastatic Melanoma Cells," Pigment Cell & Melanoma Research, vol. 30, issue 5 (May 17, 2017), pp. 1-25.

Li, Yecheng et al. "B7-H3 promotes gastric cancer cell migration and invasion," Oncotarget, vol. 8 (May 12, 2017) pp. 1-11.

Wu, Shanshan et al. "Overexpression of B7-H3 correlates with aggressive clinicopathological characteristics in nonsmall cell lung cancer," Oncotarget, vol. 7 (Nov. 7, 2016) pp. 1-7.

Wang, Gongcheng et al."Therapy to target renal cell carcinoma using I-labeled B7-H3 monoclonal antibody," Oncotarget, vol. 7, No. 17 (Apr. 2, 2016) pp. 24888-24898.

Xu, Hong et al. "B7-H3 and B7-H4 are independent predictors of a poor prognosis in patients with pancreatic cancer," Oncology Letters, vol. 11 (Jan. 19, 2016) pp. 1841-1846.

Zhao, Jia-Li et al. "B7-H3 protein expression in a murine model of osteosarcoma," Oncology Letters, vol. 12, (Jun. 2, 2016) pp. 383-386.

Zhang, Pengfei et al. "Inhibition of B7-H3 reverses oxaliplatin resistance in human colorectal cancer cells," Biochemical and Biophysical Research Communications, vol. 490, issue 3 (Aug. 26, 2017) pp. 1132-1138.

Luo, Dan et al. "B7-H3 regulates lipid metabolism of lung cancer through SREBP1-mediated expression of FASN," Biochemical and Biophysical Research Communications, vol. 482, issue 4 (Jan. 22, 2017) pp. 1246-1251.

Li, Gen et al. "B7-H3 in tumors: friend or foe for tumor immunity?," Cancer Chemotherapy and Pharmacology, vol. 81 (Jan. 3, 2018) pp. 245-253.

Xu, Hong et al. "MicroRNA miR-29 Modulates Expression of Immunoinhibitory Molecule B7-H3: Potential Implications for Immune Based Therapy of Human Solid Tumors," Cancer Research, vol. 69, issue 15 (Jul. 29, 2009) pp. 6275-6281.

Yamato, I. et al. "Clinical importance of B7-H3 expression in human pancreatic cancer," British Journal of Cancer, vol. 101 (Oct. 20, 2009) pp. 1709-1716.

Loo, Deryk et al. "Development of an Fc-Enhanced Anti-B7-H3 Monoclonal Antibody with Potent Antitumor Activity," Clinical Cancer Research, vol. 18, issue 14 (Jul. 15, 2012) pp. 3834-3845.

Chen, Lujun et al. "B7-H3 expression associates with tumor invasion and patient's poor survival in human esophageal cancer," American Journal of Translational Research, vol. 7, issue 12 (Dec. 15, 2015) pp. 2646-2660.

Loos, Martin et al. "B7-H3 and Its Role in Antitumor Immunity," Clinical and Developmental Immunology, vol. 2010, Article ID 683875 (Nov. 28, 2010) pp. 1-7.

* cited by examiner

B7-H3 ANTIBODY, ANTIGEN-BINDING FRAGMENT THEREOF AND MEDICAL USE THEREOF

CROSS REFERENCE TO RELATED APPLICATIONS

This application is a continuation of U.S. patent application Ser. No. 16/497,687, filed Sep. 25, 2019, which is a Section 371 of International Application No. PCT/CN2018/081249, filed Mar. 30, 2018, that published in the Chinese language on Oct. 4, 2018, under International Publication No. WO 2018/177393 A1, which claims priority under 35 U.S.C. § 119(b) to Chinese Application No. 201710206261.2, filed Mar. 31, 2017. The disclosures of each are incorporated herein by reference in its entirety.

REFERENCE TO SEQUENCE LISTING SUBMITTED ELECTRONICALLY

This application contains a sequence listing that was submitted electronically via EFS-Web as an ASCII formatted sequence listing with a file name "Sequence Listing_065825-104US2", creation date of Dec. 14, 2020, and having a size of about 34.5 KB. The sequence listing submitted via EFS-Web is part of the specification and is herein incorporated by reference in its entirety.

FIELD OF THE INVENTION

The present invention relates to a B7-H3 antibody or antigen-binding fragment thereof. The present invention further relates to a human antibody comprising the CDR regions of the B7-H3 antibody. The present invention also relates to a pharmaceutical composition comprising the B7-H3 antibody or antigen-binding fragment thereof, and its use as a diagnostic reagent and therapeutic agent for B7-H3 related diseases.

BACKGROUND OF THE INVENTION

The T cell-mediated immune response plays an extremely important role in anti-tumor processes of an organism, however, the activation and proliferation of T cells requires not only an antigen signal recognized by the T cell receptor (TCR), but also a second signal provided by co-stimulatory molecules. The molecules of the B7 family belong to the co-stimulatory molecule immunoglobulin superfamily. More and more studies have shown that molecules of this family play an important regulatory role in the normal immune function and pathological state in an organism.

B7-H3 is a member of B7 family and is a type I transmembrane protein, which contains a signal peptide at the amino terminus, an extracellular immunoglobulin-like variable region (IgV) and constant region (IgC), a transmembrane region, and a cytoplasmic tail region having 45 amino acids (Tissue Antigens. 2007 August; 70 (2): 96-104). B7-H3 has two kinds of splicing variants, B7-H3a and B7-H3b. The extracellular domain of B7-H3a consists of two immunoglobulin domains of IgV-IgC (also known as 2IgB7-H3), while the extracellular domain of B7-H3b consists of four immunoglobulin domains of IgV-IgC-IgV-IgC (also known as 4IgB7-H3).

B7-H3 protein is not expressed or is poorly expressed in normal tissues and cells, but highly expressed in various tumor tissues and is closely correlated with tumor progression, patient survival and prognosis. It has been clinically reported that B7-H3 is over-expressed in many types of cancers, especially in non-small cell lung cancer, renal cancer, urinary tract epithelial cancer, colorectal cancer, prostate cancer, glioblastoma multiforme, ovarian cancer and pancreas cancer (Lung Cancer. 2009 November; 66 (2): 245-249; Clin Cancer Res. 2008 Aug. 15; 14 (16): 5150-5157). In addition, it has also been reported in the literature that, in prostate cancer, the expression level of B7-H3 is positively correlated with clinical pathological malignancy (such as tumor volume, extra-prostatic invasion or Gleason score), and is also associated with cancer progression (Cancer Res. 2007 Aug. 15; 67 (16):7893-7900). Similarly, in glioblastoma multiforme, the expression of B7-H3 is inversely associated with event-free survival, and in pancreatic cancer, the expression of B7-H3 is associated with lymph node metastasis and pathological progression. Therefore, B7-H3 is considered as a new tumor marker and potential therapeutic target.

Currently, there have been therapeutic strategies specific for B7-H3 target for preclinical studies. For example, antibodies targeting murine B7-H3 will enhance infiltrative CD8-positive T cells in tumors and inhibit tumor growth (Mod Pathol. 2010 August; 23 (8): 1104-1112). Furthermore, patent WO 2008/066691 shows that antibodies recognizing the B7-H3 variant, B7-H3a, exhibited an in vivo anti-tumor effect on adenocarcinoma. In clinical studies, an ADC of murine B7-H3 antibody conjugated with radioactive I131 significantly inhibited the growth of neuroblastoma in patients (J Neufooocol 97 (3):409-18 (2010)). However, the B7H3 antibodies currently under study are humanized antibodies that have been engineered by humanization of murine antibodies. However, humanized antibodies upon immunization have higher immunogenicity than fully human antibodies which do not contain any murine antibody components. This higher immunogenicity is an unfavorable factor in human application.

Phage display technology refers to the fusion of an exogenous protein or polypeptide with a phage coat protein, so as to express an exogenous protein on the surface of the phage. The phage antibody library is an antibody library established by combining phage display technology, PCR amplification technology and protein expression technology.

The biggest advantage of the phage antibody library is to prepare the fully human antibody by mimicking the three processes of antibody production in vivo without immunization in vivo. In addition, the phage antibody library has the following advantages: 1) The unification of genotype and phenotype is achieved. In addition, the experimental method is simple and rapid. Whereas the traditional antibody production method by hybridoma technology takes several months, the antibody library technology takes only a few weeks. 2) The expressed product is a fully human antibody, and the molecular weight thereof is small. The antibody is mainly expressed in the form of active fragments Fab and scFv and when compared with complete antibody, it has obvious advantages in tissue penetrability. 3) Screening capacity is large: hybridoma technology is used to screen among thousands of clones, but antibody library technology can be used to select from millions or even hundreds of millions of molecules; therefore, more types of antibodies will be obtained. 4) Wide application: utilizing prokaryotic expression systems leads to more obvious advantage in large scale production (Curr Opin Biotechnol. 2002 December; 13 (6):598-602; Immunotechnology, 2013, 48 (13) 48 (13): 63-73).

At present, patents such as WO2008100934, WO2010096734, WO2012147713, WO2015181267, WO2016044383 etc. have reported B7-H3 antibodies, however, most of them are murine antibodies or humanized antibodies. Most of these antibodies are still in clinical phase I and discovery phase, either in domestic or overseas, and none of antibody drug targeting B7-H3 is available in market. Thus, it is necessary to further develop a B7-H3 fully human antibody with higher activity, high affinity and high stability, for the treatment of related diseases and application.

SUMMARY OF THE INVENTION

One purpose of the present invention is to provide a monoclonal antibody or antigen-binding fragment thereof that binds to the amino acid sequence(s) or three-dimensional structure of the B7-H3 extracellular region. Furthermore, another purpose of the present invention is to screen and obtain highly active and highly stable anti-human B7-H3 fully human antibodies that compete with the monoclonal antibody or antibody fragments thereof.

Furthermore, the present invention provides a DNA encoding the antibody, a vector comprising the DNA, a transformant obtained by transforming the vector, a method of producing an antibody or antibody fragment thereof using the transformant, and a diagnostic reagent or therapeutic agent in which said antibody or antibody fragment thereof is served as active ingredient.

In one aspect, the present invention provides a B7-H3 antibody or antigen-binding fragment thereof which binds to human B7-H3, wherein the B7-H3 antibody or antigen-binding fragment thereof is selected from any one of the monoclonal antibodies or antigen-binding fragments thereof of the following (i) to (ii):
(i) a monoclonal antibody or antigen-binding fragment thereof, comprising one or more CDR region sequences selected from the following sequences or selected from the amino acid sequences with at least 95% identity to the following:
  antibody heavy chain variable region HCDR sequences as shown in SEQ ID NO: 10, 11 and 12; and antibody light chain variable region LCDR sequences as shown in SEQ ID NO: 13, 14 and 15;
(ii) a monoclonal antibody or antigen-binding fragment thereof, comprising one or more CDR region sequences selected from the following sequences or selected from the amino acid sequences with at least 95% identity to the following:
  antibody heavy chain variable region HCDR sequences as shown in SEQ ID NO: 16, 17 and 18; and antibody light chain variable region LCDR sequences as shown in SEQ ID NO: 19, 20 and 21.

In a preferred embodiment, a B7-H3 antibody or antigen-binding fragment thereof according to the present invention is provided, wherein the monoclonal antibody is a recombinant antibody.

In a preferred embodiment, a B7-H3 antibody or antigen-binding fragment thereof according to the present invention is provided, wherein the monoclonal antibody is a human recombinant antibody or antigen-binding fragment thereof.

In a preferred embodiment, the B7-H3 antibody or antigen-binding fragment thereof according to the present invention is provided, wherein the framework (FR) sequences of light chain and the heavy chain variable regions of human recombinant antibody are derived from a human germline light chain and heavy chain, respectively, or mutant sequence thereof.

In a preferred embodiment, a B7-H3 antibody or antigen-binding fragment thereof according to the present invention is provided, wherein the human recombinant antibody comprises a heavy chain variable region as shown in SEQ ID NO: 6 or 8 or a variant thereof; wherein the variant has 1-10 amino acid substitution(s) in the heavy chain variable region sequence as shown in SEQ ID NO: 6 or 8.

In a preferred embodiment, a B7-H3 antibody or antigen-binding fragment thereof according to the present invention is provided, wherein the human recombinant antibody comprises a light chain variable region as shown in SEQ ID NO: 7 or 9 or a variant thereof; wherein the variant has 1-10 amino acid substitution(s) in the light chain variable region sequence of SEQ ID NO: 7 or 9.

In a preferred embodiment, a B7-H3 antibody or antigen-binding fragment thereof according to the present invention is provided, wherein the B7-H3 antibody further comprises a human antibody constant region, preferably the B7-H3 antibody is a full-length antibody consisting of the heavy chain and light chain sequence as shown in SEQ ID NO: 22 and 23, respectively; or a full-length antibody consisting of the heavy chain and light chain sequence as shown in SEQ ID NO: 22 and 26, respectively; or a full-length antibody consisting of the heavy chain and light chain sequence as shown in SEQ ID NO: 24 and 25, respectively.

In a preferred embodiment, a B7-H3 antibody or antigen-binding fragment thereof according to the present invention is provided, wherein the antigen-binding fragment is selected from the group consisting of Fab, Fab', F(ab')2, single-chain antibody (scFv), dimerized V region (diabody), disulfide-stabilized V region (dsFv) and CDR-containing peptide.

In another aspect, the present invention provides an isolated B7-H3 antibody or antigen-binding fragment thereof, characterized in that it competes with the B7-H3 antibody or antigen-binding fragment thereof as described above for binding to human B7-H3.

The present invention also provides a pharmaceutical composition comprising a therapeutically effective amount of the B7-H3 antibody or antigen-binding fragment thereof according to the present invention, and one or more pharmaceutically acceptable carrier, diluent or excipient.

The present invention also provides a nucleic acid molecule encoding the B7-H3 antibody or antigen-binding fragment thereof as described in the present invention.

The present invention also provides a recombinant vector comprising the nucleic acid molecule as described above.

The present invention also provides a host cell transformed with the recombinant vector as described above, the host cell is selected from the group consisting of prokaryotic cell and eukaryotic cell, preferably eukaryotic cell, more preferably mammalian cell or yeast cell.

The present invention also provides a method for producing the antibody or antigen-binding fragment thereof according to present invention, wherein the method includes culturing the host cell as described above in a culture to form and accumulate the B7-H3 antibody or antigen-binding fragment thereof according to present invention, and recovering the accumulated antibody or antigen-binding fragment thereof from the culture.

The present invention also provides a method for immunologically detecting or measuring B7-H3, wherein the method comprises utilizing the B7-H3 antibody or antigen-binding fragment thereof as described in the present invention.

The present invention also provides a reagent for detecting or measuring human B7-H3, wherein the reagent comprises the B7-H3 antibody or antigen-binding fragment thereof as described in the present invention.

The present invention also provides a diagnostic reagent for detecting diseases associated with B7-H3 positive cells, the diagnostic reagent comprises the B7-H3 antibody or antigen-binding fragment thereof as described in the present invention.

The present invention also provides a method for diagnosing diseases related to B7-H3 positive cells, the method comprises detecting or determining B7-H3 or B7-H3 positive cells by using the B7-H3 antibody or antigen-binding fragment thereof as described in the present invention.

In another aspect, the present invention also provides the use of the B7-H3 antibody or antigen-binding fragment thereof as described in the present invention for the preparation of a diagnostic reagent for diseases related to B7-H3 positive cells.

In another aspect, the present invention further provides a therapeutic agent for treating diseases associated with B7-H3 positive cells, the therapeutic agent comprises the B7-H3 antibody or antigen-binding fragment thereof as described in the present invention, or comprises the pharmaceutical composition as described above, or the nucleic acid molecule as described above.

The present invention also provides a method for treating diseases related to B7-H3 positive cells, the method comprises inducing cell death of B7-H3 positive cells by utilizing the antibody or antigen-binding fragment thereof as described in the present invention, or the pharmaceutical composition as described above, or the nucleic acid molecule as described above.

In another aspect, the present invention further provides the use of the antibody or antigen-binding fragment thereof, or the pharmaceutical composition, or the nucleic acid molecule as described in the present invention in the preparation of therapeutic agents for treating diseases related to B7-H3 positive cells.

BRIEF DESCRIPTION OF THE DRAWINGS

The invention may be more fully understood with reference to the accompanying drawings. The drawings are intended to illustrate, not limit, the present teachings, according to an embodiment of the present invention.

DETAILED DESCRIPTION OF THE INVENTION

Terms

Figure 1:
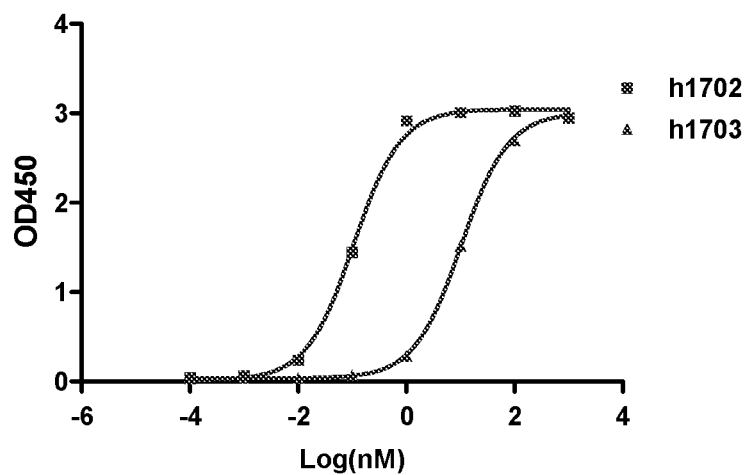
FIG. 1: Binding ability of different antibodies to human 2Ig-B7-H3 antigen.

In order to more readily understand the present invention, certain technical and scientific terms are specifically defined below. Unless specifically indicated elsewhere in this document, all other technical and scientific terms used herein have the meaning commonly understood by one of ordinary skill in the art to which this invention pertains.

As used herein, the three-letter code and the single-letter code for amino acids are as described in J. biol. chem, 243, p 3558 (1968).

As used herein, "antibody" refers to immunoglobulin, a structure of four-peptide chains connected together by disulfide bonds between two identical heavy chains and two identical light chains. Different immunoglobulin heavy chain constant regions exhibit different amino acid compositions and rank orders, hence present different kinds of antigenicity. Accordingly, immunoglobulin can be divided into five categories, or immunoglobulin isotypes, namely IgM, IgD, IgG, IgA and IgE, with heavy chain $\mu$, $\delta$, $\gamma$, $\alpha$ and $\epsilon$, respectively. According to its amino acid composition of the hinge region and the number and location of heavy chain disulfide bonds, the same type of Ig can be divided into different sub-categories. For example, IgG can be divided into IgG1, IgG2, IgG3, and IgG4. Light chains can be divided into $\kappa$ or $\lambda$ chain, due to different constant regions. Each IgG among the five types has $\kappa$ or $\lambda$ chain.

In the present invention, the antibody light chain as described herein further comprises a light chain constant region, wherein the light constant region comprises a human or murine $\kappa$, $\lambda$ chain or a variant thereof.

In the present invention, the antibody heavy chain as described herein further comprises a heavy chain constant region, wherein the heavy chain constant region comprises human or murine IgG1, IgG2, IgG3, IgG4 or a variant thereof.

The sequence of about 110 amino acids closest to the N-terminus of the antibody heavy and light chains, changes largely, known as the variable region (Fv region). The sequence of amino acids closest to the C-terminus is relatively stable, known as constant region. The variable region comprises three hypervariable regions (HVR) and four framework regions (FR) having relatively conserved sequences. Three hypervariable regions determine the specificity of the antibody, also known as complementarity determining regions (CDRs). Each light chain variable region (LCVR) and each heavy chain variable region (HCVR) comprises three CDR regions and four FR regions. Sequentially ordered from the amino terminus to the carboxyl terminus is: FR1, CDR1, FR2, CDR2, FR3, CDR3, and FR4. The three-light chain CDRs are referred to as LCDR1, LCDR2, and LCDR3. The three-heavy chain CDRs are referred to as HCDR1, HCDR2 and HCDR3. The number and location of the CDR amino acid residues in the LCVR and HCVR regions of the antibody or antigen binding fragment herein comply with known Kabat numbering criteria (e.g., LCDR1-3, HCDR2-3), or comply with Kabat and Chothia numbering criteria (e.g., HCDR1).

The terms "human antibody" and "human derived antibody" are used interchangeably and refer to an antibody comprising one or more variable and constant regions derived from a human immunoglobulin sequence. In a preferred embodiment of the invention, all of the variable and constant regions are derived from human immunoglobulin sequences, i.e., "fully human derived antibody" or "fully human antibody". These antibodies can be obtained in a variety of ways, including antibodies obtained by using phage display technology, including isolating B cells from human PBMC, spleen, lymph node tissue and constructing natural single-stranded phage human antibody library, or by immunizing transgenic mice expressing human antibody light and heavy chain and screening.

The term "murine antibody" used in the present invention refers to a monoclonal antibody against human B7-H3 prepared according to the knowledge and skill in the art.

During preparation, the test subject is injected with a B7-H3 antigen, and then the hybridoma expressing antibodies having desired sequences or functional properties are isolated. In a preferred embodiment of the invention, the murine B7-H3 antibody or antigen-binding fragment thereof further comprises a light chain constant region of a murine kappa, lambda chain or a variant thereof, or further comprises a heavy chain constant region of murine IgG1, IgG2, IgG3 or variants thereof.

The term "chimeric antibody" is an antibody which is formed by fusing the variable region of a murine antibody with the constant region of a human antibody, so as to alleviate the murine antibody-induced immune response. To establish a chimeric antibody, a hybridoma secreting a specific murine monoclonal antibody is established and a variable region gene is cloned from the murine hybridoma cells. Then a desired constant region gene of a human antibody is cloned and connected with the murine variable region genes to form a chimeric gene which can be subsequently inserted into an expression vector. Finally, the chimeric antibody molecule is expressed in eukaryotic or prokaryotic system. In a preferred embodiment of the present invention, the light chain of the B7-H3 chimeric antibody further comprises a light chain constant region derived from the human kappa, lambda chain or a variant thereof. The heavy chain of the B7-H3 chimeric antibody further comprises a heavy chain constant region derived from human IgG1, IgG2, IgG3 or IgG4 or a variant thereof, and preferably comprises a heavy chain constant region derived from human IgG1, IgG2 or IgG4, or variant of IgG1, IgG2 or IgG4 with amino acid mutations (such as YTE mutation or back mutation).

The term "humanized antibody," also known as CDR-grafted antibody, refers to an antibody generated by grafting murine CDR sequences into a variable region framework of a human antibody (i.e., antibodies produced within different types of human germline antibody framework sequences). A humanized antibody overcomes the heterologous response induced by a chimeric antibody that carries a large amount of murine protein components. Such framework sequences can be obtained from public DNA databases including germline antibody gene sequences or published references. For example germline DNA sequences of human heavy and light chain variable region genes can be found in e.g., "VBase" human germline sequence database (available on the Internet at www.mrccpe.com.ac.uk/vbase), as well as found in Kabat, E A, et al, 1991 Sequences of Proteins of Immunological Interest, 5th edition.

The CDR graft can reduce the affinity of the B7-H3 antibody or antigen-binding fragment thereof to the antigen, due to the framework residues that are in contact with the antigen. Such interaction can be the result of hyper-mutation in somatic cells. Therefore, it may still be necessary to graft such donor framework amino acids onto the framework of humanized antibodies. Amino acid residues from a non-human B7-H3 antibody or antigen-binding fragment thereof which are involved in antigen binding can be identified by examining the murine monoclonal antibody variable region sequences and structures. Each residue in the CDR donor framework that differs from the germline can be considered to be relevant. If the closest germline cannot be determined, the sequence can be compared with the common sequence of a subtype or the sequence of the murine with a high similarity percentage. Rare framework residues are thought to be the result of somatic hyper-mutation and thus play an important role in binding.

The term "antigen-binding fragment" or "functional fragment" of an antibody refers to one or more fragments of an antibody that retain the ability to specifically bind to an antigen (e.g., B7-H3). It has been shown that fragments of full-length antibodies can be used for the antigen-binding function of antibodies. Examples of the binding fragments included in the term "antigen-binding fragment" of an antibody include: (i) Fab fragment, a monovalent fragment consisting of VL, VH, CL and CH1 domains; (ii) F(ab')2 fragment, a bivalent fragment comprising two Fab fragments linked by disulfide bonds in the hinge region, (iii) Fd fragment, consisting of the VH and CH1 domains; (iv) Fv fragment, consisting of the VH and VL domains of one arm of the antibody; (v) single domain or dAb fragment (Ward et al. (1989) Nature 341: 544-546) composed of the VH domain; and (vi) a separate complementarity determining region (CDR); or (vii) a combination of two or more separated CDRs optionally linked by a synthetic linker. Furthermore, although the VL domain and VH domain of the Fv fragment are encoded by separate genes, they can be linked by a synthetic linker using recombinant methods such that they can generate a single protein chain with monovalent molecular structure by pairing the VL and VH domains (called single-chain Fv (scFv); see, e.g., Bird et al. (1988) Science 242: 423-426; and Huston et al. (1988) Proc. Natl. Acad. Sci USA 85: 5879-5883). Such single chain antibodies are also intended to be included in the term "antigen-binding fragment" of an antibody. Such antibody fragments are obtained using conventional techniques known in the art, and functional screening of fragments are used in the same way as the intact antibodies. The antigen binding sites can be produced by recombinant DNA techniques or by enzymatic or chemical disruption of the intact immunoglobulin. The antibodies may be in different phenotype, e.g., IgG (e.g., IgG1, IgG2, IgG3 or IgG4 subtype), IgA1, IgA2, IgD, IgE or IgM antibody.

The antigen-binding fragments of the present invention include Fab, F(ab')2, Fa', single-chain antibody (scFv), dimerized V region (diabody), disulfide-stabilized V region (dsFv), CDR-containing peptide, etc.

Fab is an antibody fragment having a molecular weight of about 50,000 and having antigen-binding activity, such fragments are obtained by treating an IgG antibody molecule with protease papain (cleaving amino acid residue at position 224 of H chain), wherein about half of the N-terminal side of the H chain and the entire L chain are bound by disulfide bond.

The Fab of the present invention can be produced by treating the monoclonal antibodies of the present invention, which specifically recognizes human B7-H3 and binds to the extracellular region amino acid sequence or three-dimensional structure thereof, with papain. Furthermore, the Fab can be produced by inserting a DNA encoding Fab of the antibody into a prokaryotic expression vector or eukaryotic expression vector and introducing the vector into prokaryote or eukaryote to express the Fab.

F(ab')2 is an antibody fragment obtained by digesting the lower part of two disulfide bonds in IgG hinge region with pepsin. It has a molecular weight of about 100,000 and antigen-binding activity and comprises two Fab regions linked at the hinge position.

The F(ab')2 of the present invention can be produced by treating the monoclonal antibody of the present invention that specifically recognizes human B7-H3 and binds to the extracellular region amino acid sequence or three-dimensional structure thereof, with pepsin. Furthermore, the F(ab')2 can be produced by linking the Fab' described below with a thioether bond or a disulfide bond.

Fab' is an antibody fragment having a molecular weight of about 50,000 and having antigen-binding activity. It is obtained by cleaving the disulfide bond in the hinge region of the F(ab')2 mentioned above. The Fab' of the present invention may be produced by treating the F(ab')2 of the present invention that specifically recognizes human B7-H3 and binds to the extracellular region amino acid sequence or three-dimensional structure thereof, with a reducing agent (such as dithiothreitol).

Furthermore, the Fab' can be produced by inserting a DNA encoding a Fab' fragment of the antibody into a prokaryotic expression vector or a eukaryotic expression vector and introducing the vector into prokaryote or eukaryote to express the Fab'.

The term "single-chain antibody," "single-chain Fv," or "scFv" refers to a molecule comprising an antibody heavy chain variable domain (or region; VH) and an antibody light chain variable domain (or region; VL) connected by a linker. Such scFv molecules have the general structure: NH2-VL-linker-VH—COOH or NH2-VH-linker-VL-COOH. Suitable linkers in prior art consist of repeated GGGGS amino acid sequence or variants thereof, for example a variant having 1-4 repeats (Holliger et al. (1993), Proc. Natl. Acad. Sci. USA 90: 6444-6448). Other linkers that can be used in the present invention are described in Alfthan et al. (1995), Protein Eng. 8: 725-731, Choi et al. (2001), Eur. J. Immunol. 31: 94-106, Hu et al. (1996), Cancer Res. 56: 3055-3061, Kipriyanov et al. (1999), J. Mol. Biol. 293: 41-56 and Roovers et al. (2001), Cancer Immunol.

The scFv of the present invention can be produced by the following steps: obtaining the cDNA encoding VH and VL of the monoclonal antibody of the present invention which specifically recognizes human B7-H3 and binds to the extracellular region amino acid sequence or three-dimensional structure thereof; constructing a DNA encoding the scFv; inserting the DNA into a prokaryotic expression vector or a eukaryotic expression vector; and then introducing the expression vector into prokaryote or eukaryote to express said scFv.

A diabody is an antibody fragment in which the scFv is dimerized and is an antibody fragment having bivalent antigen-binding activity. In the bivalent antigen binding activity, the two antigens may be the same or different.

The diabody of the present invention can be produced by the following steps: obtaining the cDNA encoding VH and VL of the monoclonal antibody of the present invention that specifically recognizes human B7-H3 and binds to the extracellular region amino acid sequence or three-dimensional structure thereof; constructing a DNA encoding scFv such that the length of the linker peptide is 8 or less amino acid residues; inserting the DNA into a prokaryotic expression vector or a eukaryotic expression vector; and then introducing the expression vector into prokaryote or eukaryote to express the diabody.

The dsFv is obtained by substituting one amino acid residue in each of the VH and the VL with cysteine residue, and then linking the polypeptides via disulfide bond between the two cysteine residues. The amino acid residue to be substituted with a cysteine residue can be selected based on a three-dimensional structure prediction of the antibody in accordance with known methods (Protein Engineering, 7, 697 (1994)).

The dsFv of the present invention can be produced by the following steps: obtaining the cDNA encoding the VH and the VL of the monoclonal antibody of the present invention that specifically recognizes human B7-H3 and binds to the extracellular region amino acid sequence or three-dimensional structure thereof; constructing a dsFv-encoding DNA; inserting the DNA into prokaryotic expression vector or eukaryotic expression vector; and then introducing the expression vector into prokaryote or eukaryote to express said dsFv.

The CDR-containing peptide is constructed by one or more regions of CDRs of VH or VL. Peptides comprising several CDRs can be linked directly or via a suitable peptide linker.

The CDR-containing peptide of the present invention can be produced by the following steps: constructing a DNA encoding CDRs of the VH and the VL of the monoclonal antibody of the present invention which specifically recognizes human B7-H3 and binds to the extracellular region amino acid sequence or three-dimensional structure thereof; inserting the DNA into a prokaryotic expression vector or a eukaryotic expression vector; and then introducing the expression vector into prokaryote or eukaryote to express said peptide. The CDR-containing peptide can also be produced by chemical synthesis methods such as Fmoc method or tBoc method.

The term "CDR" refers to one of the six hypervariable regions within the variable domain of an antibody that primarily contributes to antigen binding. One of the most commonly used definitions for the six CDRs is provided by Kabat E. A. et al. (1991) Sequences of proteins of immunological interest. NIH Publication 91-3242. As used herein, the Kabat definition of CDR only applies to CDR1, CDR2 and CDR3 of the light chain variable domain (CDR L1, CDR L2, CDR L3 or L1, L2, L3), as well as CDR2 and CDR3 of heavy chain variable domain (CDR H2, CDR H3 or H2, H3).

The term "antibody framework" as used herein, refers to a portion of the variable domain VL or VH, which serves as a scaffold for the antigen binding loop (CDR) of the variable domain. Essentially, it is a variable domain without CDRs.

The term "epitope" or "antigenic determinant" refers to a site on an antigen to that an immunoglobulin or antibody specifically binds (e.g., a specific site on B7-H3 molecule). Epitopes typically include at least 3, 4, 5, 6, 7, 8, 9, 10, 11, 12, 13, 14 or 15 contiguous or non-contiguous amino acids in a unique spatial conformation. See, for example, Epitope Mapping Protocols in Methods in Molecular Biology, Vol. 66, G. E. Morris, Ed. (1996).

The terms "specific binding," "selective binding," "selectively bind," and "specifically bind" refer to the binding of an antibody to an epitope on a predetermined antigen. Typically, the antibody binds with an affinity (KD) of less than about 10-7 M, such as approximately less than about 10-8 M, 10-9 M or 10-10 M or less.

The term "KD" or "Kd" refers to the dissociation equilibrium constant for a particular antibody-antigen interaction. Typically, the antibody of the present invention binds to B7-H3 with a dissociation equilibrium constant (KD) of less than about 10-7 M, such as less than about 10-8 M, 10-9 M or 10-10 M or less, for example, as determined using surface plasmon resonance (SPR) techniques in a BIACORE instrument.

The term "competitive binding" refers to an antibody that recognizes and binds to the same epitope (also known as antigenic determinant) or a portion thereof of the extracellular domain of human B7H3 as the one recognized by monoclonal antibody of the present invention. An antibody that binds to the same epitope as the monoclonal antibody of the present invention refers to an antibody that recognizes and binds to the amino acid sequence of human B7-H3 recognized by the monoclonal antibody of the present invention.

The term "nucleic acid molecule" as used herein refers to a DNA molecule and a RNA molecule. The nucleic acid molecule may be single stranded or double stranded but is preferably a double stranded DNA. A nucleic acid is "effectively linked" when it is placed into functional relationship with another nucleic acid sequence. For example, if a promoter or enhancer affects transcription of a coding sequence, the promoter or enhancer is effectively linked to the coding sequence.

The term "vector" refers to a nucleic acid molecule capable of transporting another nucleic acid to that it has been linked. In one embodiment, the vector is a "plasmid" that refers to a circular double stranded DNA loop into which additional DNA segment can be ligated. In another embodiment, the vector is a viral vector, wherein an additional DNA segment can be ligated into viral genome. The vectors disclosed herein are capable of self-replicating in a host cell into which they have been introduced (for example, a bacterial vector having a bacterial replication origin and a episomal mammalian vector) or can be integrated into the genome of a host cell upon introduction into host cell, thereby is replicated along with the host genome (e.g., a non-episomal mammalian vector).

Methods for producing and purifying antibodies and antigen-binding fragments are well known in the art, such as Cold Spring Harbor Antibody Technical Guide, Chapters 5-8 and 15. For example, mice can be immunized with human B7-H3 or a fragment thereof, and the obtained antibody can be re-natured, purified, and sequenced by using conventional methods known in the art. The antigen-binding fragment can also be prepared by conventional methods. The antibodies or antigen-binding fragments of the invention are genetically engineered to add one or more human FR regions in non-human CDR regions. The human FR germline sequence(s) can be obtained by aligning human antibody variable germlines in gene databases and MOE software from the ImMunoGeneTics (IMGT) website at http://imgt.cines.fr or from the Journal of Immunoglobulins 2001ISBN012441351.

The term "host cell" refers to a cell into which an expression vector has been introduced. Host cells can include bacterial, microbial, plant or animal cells. Bacteria susceptible to be transformed include members of the Enterobacteriaceae family, such as strains of *Escherichia coli* or *Salmonella*; Bacillaceae such as *Bacillus subtilis*; Pneumococcus; Streptococcus and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibody or antigen-binding fragment of the present invention can be prepared and purified by conventional methods. For example, cDNA sequence(s) encoding a heavy chain and a light chain can be cloned and recombined into a GS expression vector. The recombinant immunoglobulin expression vector can be stably transfected in CHO cells., Mammalian expression systems result in glycosylation of antibodies, particularly at the highly conserved N-terminal site in the Fc region. Stable clones are obtained by expressing antibodies that specifically bind to human B7-H3. Positive clones are expanded in serum-free medium in a bioreactor to produce antibodies. The culture medium containing the secreted antibody can be purified by conventional technique. For example, purification is carried out using an A or G Sepharose FF column that has been equilibrated with a compatible buffer. The non-specifically bound components are removed by washing. The bound antibody is eluted by a pH gradient method, and the antibody fragments are detected by SDS-PAGE and collected. The antibody can be filtered and concentrated by a conventional manner. Soluble aggregate and multimers can also be removed by conventional methods such as size exclusion or ion exchange. The product needs to be frozen immediately, such as at −70° C., or lyophilized.

"Administration" and "treatment," when applied to an animal, human, experimental subject, cell, tissue, organ, or biological fluid, refer to contact with an exogenous pharmaceutical, therapeutic, diagnostic reagent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting the cell with a reagent, as well as contacting a fluid with a reagent, wherein the fluid is in contact with the cell. "Administration" and "treatment" also mean in vitro and ex vivo treatments, e.g., of a cell, by a reagent, diagnostic, binding composition or by another cell. "Treatment," when applied to a human, veterinary, or research subject, refers to therapeutic treatment, prophylactic or preventative measures, research and diagnostic applications.

"Treat" means to administer a therapeutic agent, such as a composition comprising any of the binding compounds of the present invention, internally or externally to a patient having one or more disease symptoms for which the agent has known therapeutic activity. Typically, the agent is administered in an amount effective to alleviate one or more disease symptoms in the treated patient or population, so as to induce the regression of such symptom(s) or to prevent the progression by any clinically measurable degree. The amount of a therapeutic agent that is effective to alleviate any particular disease symptom (also referred to "therapeutically effective amount") may vary according to factors such as the disease state, age and weight of the patient, and the ability of the agent to elicit desired response in the patient. Whether a disease symptom has been alleviated can be assessed by any clinical measurement typically used by physicians or other skilled healthcare providers to assess the severity or progression status of that symptom. Even if an embodiment of the present invention (e.g., a treatment method or article of manufacture) is not effective in alleviating the target disease symptom(s) in every patient, it should alleviate the target disease symptom(s) in a statistically significant number of patients as determined by any statistical test known in the art such as the Student's t-test, chi-square test, U-test according to Mann and Whitney, Kruskal-Wallis test (H-test), Jonckheere-Terpstra test and Wilcoxon test.

"Conservative modification" or "conservative replacement or substitution" refers to substitutions of amino acids in a protein with other amino acid having similar characteristics (e.g., charge, side chain size, hydrophobicity/hydrophilicity, backbone conformation and rigidity, etc.), such that the changes can be frequently made without altering the biological activity of the protein. It will be appreciated by those skilled in the art that, in general, a single amino acid substitution in a non-essential region of polypeptide does not substantially alter biological activity (see, for example, Watson et al. (1987) Molecular Biology of the Gene, The Benjamin/Cummings Pub. Co., Page 224, (4th edition)). In addition, substitutions with structurally or functionally similar amino acids are unlikely to disrupt biological activity.

An "effective amount" includes an amount sufficient to ameliorate or prevent a symptom or condition of medical disease. An effective amount also means an amount sufficient to allow or facilitate the diagnosis. An effective amount for a particular patient or veterinary subject can vary depending on factors such as: the condition to be treated, the overall health condition of the patient, the route and dose of administration, and the severity of side effects. An effective amount can be the maximum dose or dosing regimen that avoids significant side effects or toxic effects.

"Exogenous" refers to a substance that is produced outside of organism, cell or human, depending on the situation. "Endogenous" refers to a substance that is produced in a cell, organism or human, depending on the situation.

"Identity" refers to the sequence similarity between two polynucleotide sequences or two polypeptide sequences. When the positions in two sequences to be compared are occupied by the same base or amino acid monomer subunit, for example, if each position of two DNA molecules is both occupied by adenine, the molecules are considered to be homologous at that position. The percent identity between the two sequences is a function of the number of matched or homologous positions shared by two sequences divided by the number of positions to be compared ×100. For example, in the optimal alignment of sequence(s), if there are 6 matches or homologs among 10 positions between two sequences, then the two sequences are deemed as having 60% homology; if there are 95 matches or homologs among 100 positions between two sequences, then the two sequences are deemed as having 95% homology. In general, a comparison is performed when the maximum identity percentage is obtained by aligning two sequences.

As used herein, the expressions "cell," "cell line," and "cell culture" are used interchangeably, and all such terms include the progeny thereof. Thus, the words "transformant" and "transformed cell" include primary test cells and cultures derived therefrom, regardless of the number of passages. It should also be understood that all progeny may not be exactly identical in terms of DNA content due to deliberate or inadvertent mutations. The mutant progeny having the same function or biological activity as screened for the primarily transformed cell is included. In the case of a different name, it is clearly understood from the context.

As used herein, "polymerase chain reaction" or "PCR" refers to a procedure or technique in that small amount of particular portion of nucleic acid, RNA, and/or DNA are amplified as described for example in U.S. Pat. No. 4,683, 195. In general, it is necessary to obtain sequence information from the end or beyond the target region, thereby oligonucleotide primers can be designed; these primers are identical or similar to the opposite strands of the template to be amplified. The 5' terminal nucleotides of the two primers may be identical to the ends of the material to be amplified. PCR can be used to amplify specific RNA sequences, specific DNA sequences from total genomic DNA, and cDNA transcribed from total cellular RNA, phage or plasmid sequences, etc. See generally, Mullis et al. (1987) Cold Spring Harbor Symp. Ouant. Biol. 51:263; Erlich ed., (1989) PCR TECHNOLOGY (Stockton Press, N.Y.). The PCR used herein is considered as an example (but not the only one) of nucleic acid polymerase reaction method for amplifying a nucleic acid test sample, said method comprises the use of known nucleic acids as a primer and nucleic acid polymerase to amplify or produce a specific portion of the nucleic acid.

"Optional" or "optionally" means that the event or situation described subsequently may (but need not to) occur, this includes where the event or situation occurs or does not occur. For example, "optionally comprising 1-3 antibody heavy chain variable regions" means that the antibody heavy chain variable region with specific sequence can be, but need not to, be present.

"Pharmaceutical composition" means a mixture comprising one or more compounds described herein or a physiologically/pharmaceutically acceptable salt or prodrug thereof, along with other chemical components, such as physiological/pharmaceutically acceptable carrier and excipient. The purpose of the pharmaceutical composition is to promote the administration to the organism and facilitate the absorption of active ingredient and thereby exert a biological activity.

Furthermore, the present invention relates to a method for immunologically detecting or measuringB7-H3, a reagent for immunologically detecting or measuring B7-H3, a method for immunologically detecting or measuring cells expressing B7-H3, and a diagnostic reagent for diagnosis of disease related to B7-H3 positive cells, comprising the monoclonal antibody or antibody fragment of the present invention that specifically recognizes human B7-H3 and binds to extracellular region amino acid sequence or three-dimensional structure thereof, as an active ingredient.

In the present invention, the method for detecting or determining the amount of B7-H3 may be any known method. For example, it includes immunodetection or assay.

The immunodetection or assay is a method of detecting or determining the amount of antibody or antigen by using labeled antigen or antibody. Examples of immunodetection or assay include a radioactive substance labeled immunological antibody method (MA), an enzyme immunoassay (EIA or ELISA), a fluorescent immunoassay (FIA), a luminescent immunoassay, a western blotting method, physicochemical methods, etc.

The above-mentioned diseases related to B7-H3 positive cells can be diagnosed by detecting or measuring cells expressing B7-H3 by using the monoclonal antibodies or antibody fragments thereof of the present invention.

In order to detect cells expressing the polypeptide, a known immunodetection can be used, and preferably immunoprecipitation, fluorescent cell staining or immunohistochemical staining etc. can be used. Furthermore, a fluorescent antibody staining method etc. using FMAT8100HTS system (Applied Biosystem) can be used.

In the present invention, a living sample for detecting or measuring B7-H3 is not particularly limited, so as long as it has a possibility of including cells expressing B7-H3, such as tissue cells, blood, plasma, serum, pancreatic fluid, urine, feces, tissue fluid or culture fluid.

The diagnostic reagent containing the monoclonal antibody or the antibody fragment thereof of the present invention may further contain a reagent for performing antigen-antibody reaction or a reagent for detecting the reaction, depending on desired diagnostic method. The reagent for performing antigen-antibody reaction includes buffers, salts, and the like. The reagent for detection includes reagents commonly used in immunodetection or measurement, such as labeled secondary antibodies that recognize the monoclonal antibodies, antibody fragments or conjugates thereof, substrates corresponding to the labels, etc.

The present invention also relates to a method of treating diseases related to human B7-H3 positive cells, particularly in the treatment of cancer and inflammation.

EXAMPLES

The present invention is further described below in conjunction with the example, however the scope of the present invention is not limited thereto. In the examples of the present invention, where specific conditions are not described, the experiments are generally conducted under conventional conditions as described in Cold Spring Harbor Antibody Technology Laboratory Manual, Molecular Cloning Manual, or under conditions recommended by the manufacturer of raw material or products. Where the source of the reagents is not specifically given, the reagents are commercially available conventional reagents.

Example 1

Preparation of B7-H3 Antigen and Protein for Detection

Design of B7-H3 antigen: The human B7-H3 sequence as shown in SEQ ID NO: 1 was used as the template for B7-H3 of the present invention, and the amino acid sequence of the antigen and protein for detection involved in the present invention were designed. Unless otherwise specified, the following B7-H3 antigen is human B7-H3.

Human B7-H3 full-length amino acid sequence (SEQ ID NO: 1):

MLRRRGSPGMGVHVGAALGALWFCLTGALEVQVPEDPVVALVGTDATLCCS
FSPEPGFSLAQLNLIWQLTDTKQLVHSFAEGQDQGSAYANRTALFPDLLAQ
GNASLRLQRVRVADEGSFTCFVSIRDFGSAAVSLQVAAPYSKPSMTLEPNK
DLRPGDTVTITCSSYQGYPEAEVFWQDGQGVPLTGNVTTSQMANEQGLFDV
HSILRVVLGANGTYSCLVRNPVLQQDAHSSVTITPQRSPTGAVEVQVPEDP
VVALVGTDATLRCSFSPEPGFSLAQLNLIWQLTDTKQLVHSFTEGRDQGSA
YANRTALFPDLLAQGNASLRLQRVRVADEGSFTCFVSIRDFGSAAVSLQVA
APYSKPSMTLEPNKDLRPGDTVTITCSSYRGYPEAEVFWQDGQGVPLTGNV
TTSQMANEQGLFDVHSVLRVVLGANGTYSCLVRNPVLQQDAHGSVTITGQP
MTFPPEALWVTVGLSVCLIALLVALAFV*CWRKIKQSCEEENAGAEDQDGEG*
*EGSKTALQPLKHSDSKEDDGQEIA*

Note:
The double-underlined portion is the signal peptide (Signal peptide: 1-28);

The underlined portion is the B7-H3 extracellular domain (Extracellular domain: 29-466), wherein 29-139 is Ig-like V-type 1 Domain, and 145-238 is Ig-like C2-type 1 Domain; 243-357 is Ig-like V-type 2 Domain, 363-456 is Ig-like C2-type 2 Domain.

The dot-lined portion is the transmembrane domain portion (Transmembrane domain: 467-487).

The italic portion is the intracellular domain (Cytoplasmic domain: 488-534).

Murine B7-H3 full-length amino acid sequence (SEQ ID NO: 2)

MLRGWGGPSVGVCVRTALGVLCLCLTGAVEVQVSEDPVVALVDTDATLRCS
FSPEPGFSLAQLNLIWQLTDTKQLVHSFTEGRDQGSAYSNRTALFPDLLVQ
GNASLRLQRVRVTDEGSYTCFVSIQDFDSAAVSLQVAAPYSKPSMTLEPNK
DLRPGNMVTITCSSYQGYPEAEVFWKDGQGVPLTGNVTTSQMANERGLFDV
HSVLRVVLGANGTYSCLVRNPVLQQDAHGSVTITGQPLTFPPEALWVTVGL
SVCLVVLLVALAFV*CWRKIKQSCEEENAGAEDQDGDGEGSKTALRPLKPSE*
*NKEDDGQEIA*

Note:
The double-underlined portion is the signal peptide (Signal peptide: 1-28);

The underlined portion is the B7-H3 extracellular domain (Extracellular domain: 29-248), wherein 29-139 is Ig-like V-type Domain, and 145-238 is Ig-like C2-type Domain.

The dot-lined portion is the transmembrane domain portion (Transmembrane domain: 249-269).

The italic portion is the intracellular domain (Cytoplasmic domain: 270-316).

The human B7-H3 antigen (SEQ ID NO: 3) used for screening and detection is a commercial product (R&D cat #1949-B3-050/CF, abbreviated as 2Ig-B7-H3), and the sequence is as follows:

LEVQVPEDPVVALVGTDATLCCSFSPEPGFSLAQLNLIWQLTDTKQL
VHSFAEGQDQGSAYANRTALFPDLLAQGNASLRLQRVRVADEGSFTC
FVSIRDFGSAAVSLQVAAPYSKPSMTLEPNKDLRPGDTVTITCSSYQ
GYPEAEVFWQDGQGVPLTGNVTTSQMANEQGLFDVHSILRVVLGANG
TYSCLVRNPVLQQDAHSSVTITPQRSPTG-*HHHHHH*

Note:
The underlined portion is the B7-H3 extracellular region; the italic portion is the His-tag marker.

The human B7-H3 antigen (SEQ ID NO: 4) used for detection is a commercial product (SinoBiological cat #11188-H08H, abbreviated as 4Ig-B7-H3), and the sequence is as follows:

LEVQVPEDPVVALVGTDATLCCSFSPEPGFSLAQLNLIWQLTDTKQLVHS
FAEGQDQGSAYANRTALFPDLLAQGNASLRLQRVRVADEGSFTCFVSIRD
FGSAAVSLQVAAPYSKPSMTLEPNKDLRPGDTVTITCSSYQGYPEAEVFW
QDGQGVPLTGNVTTSQMANEQGLFDVHSILRVVLGANGTYSCLVRNPVLQQ
DAHSSVTITPQRSPTGAVEVQVPEDPVVALVGTDATLRCSFSPEPGFSLA
QLNIWQLTDTKQLVHSFTEGRDQGSAYANRTALFPDLLAQGNASLRLQRV
RVADEGSFTCFVSIRDFGSAAVSLQVAAPYSKPSMTLEPNKDLRPGDTVT
ITCSSYRGYPEAEVFWQDGQGVPLTGNVTTSQMANEQGLFDVHSVLRVVL
GANGTYSCLVRNPVLQQDAHGSVTITGQPMT-*HHHHHH*

Note:
The underlined portion is the B7-H3 extracellular region; the italic portion is the His-tag marker.

The murine B7-H3 antigen (SEQ ID NO: 5) used for screening and detection is a commercial product (R&D cat #1397-B3-050/CF), and the sequence is as follows:

VEVQVSEDPVVALVDTDATLRCSFSPEPGFSLAQLNLIWQLTDTKQLVHF
TEGRDQGSAYSNRTALFPDLLVQGNASLRLQRVRVTDEGSYTCFVSIQDF
DSAAVSLQVAAPYSKPSMTLEPNKDLRPGNMVTITCSSYQGYPEAEVFWK

-continued

DGQGVPLTGNVTTSQMANERGLFDVHSVLRVVLGANGTYSCLVRNPVLQQ

DAHGSVTITGQPLTF-*HHHHHH*

Note:
The underlined portion is the B7-H3 extracellular region; the italic portion is the His-tag marker.

Example 2

Screening Positive Sequence(s) for Specific Binding to Human B7-H3

B cells were isolated from human peripheral blood mononuclear cells (PBMCs), spleen, and lymph node tissues, and RNA was extracted to construct naive scFv phage antibody library (capacity 3.2×10$^{10}$). The constructed naive scFv phage antibody library was packaged to form phage particles, and then subjected to panning by liquid phase method. The phage was bound to the biotinylated B7-H3 in liquid phase, and then was separated by streptavidin magnetic beads. In order to obtain positive sequence(s) binding to human B7-H3 (R&D cat #1949-B3-050/CF), biotinylated human B7-H3 was used for panning, and 500 monoclonal colonies were picked and packaged into phage scFv antibodies for phage ELISA testing. The binding activity of monoclonal phage to human B7-H3 (R&D cat #1949-B3-050/CF) and murine B7-H3 (R&D cat #1397-B3-050/CF) were tested separately: 1 μg/ml human B7-H3 or murine B7-H3 and 1% BSA were coated on ELISA plate, phage supernatant diluted at 1:1 with blocking buffer was added, and detected with anti-M13 HRP; the clones with ELISA OD450 value of greater than 0.5, and with ratios of ELISA OD450 values for binding with human or murine B7-H3 to ELISA OD450 value for binding with 1% BSA greater than 2.0 were selected, and 9 clones were obtained.

Example 3

Construction of Full Length Monoclonal Antibodies

Full length antibodies were constructed for these 9 clones obtained by phage library screening, and then two antibodies (h1702 and h1703, respectively) were confirmed to have strong affinity by ELISA binding assay. The process of constructing full length monoclonal antibody was as follows:

Based on the scFv antibody sequence(s) obtained by phase screening, primers were designed to construct the VH/VK/VL gene fragment of each single-chain antibody sequence by PCR. The heavy and light chain variable regions of h1702 and h1703 were obtained.

>h1702 heavy chain variable region sequence

SEQ ID NO: 6
*QVQLVQSGGGVVQPGTSLRLSCAA*SGFIFSSSA*MHWVRQAPGKGLEW*

*VAVI*SYDGSNKY*YDSVKGRFTISRDNSKNTLYLQMNSLRAEDTAVYY*

*C*ARSARLYASFDY*WGQGALVTVSS*

>h1702 light chain variable region sequence

SEQ ID NO: 7
*QTVVTQESFSVSPGGTVTLTCGLS*SGSVSTSHY*PSWYQQTPGQAPRML*

*AIY*NTN*TRSSGVPDRFSGSILGNKAALTITGAQADDESDYYC*AIHVD

RDIWV*FGGGTKLTVL*

>h1703 heavy chain variable region sequence

SEQ ID NO: 8
QVQLQESGGGLVQPGGSLRLSCAASGFTFSSYAMSWVRQAPGKGLEWV

SAISGSGGSTYYADSVKGRYTISRDNSKNTLYLQMNSLRAEDTAVYYC

AKGVGPHALDVWGQGTTVTVSS

>h1703 light chain variable region sequence

SEQ ID NO : 9
DIRLTQSPSSLSASVGDRVTTTCRASQSISTYLNWYQQKPGKAPILLIN

AVSGLQSGVPSRFSGSGSGTHFTLTITISLQPEDFATYYCQQSYSTPMW

TFGQGTKVEIK

Note: The order is FR1-CDR1-FR2-CDR2-FR3-CDR3-FR4, the italics in sequence are FR sequences, and the CDR sequences are underlined.

The CDR sequences in the light chain and heavy chain of each antibody are shown in Table 1.

TABLE 1

| CDR regions of each heavy and light chain | | | | |
|---|---|---|---|---|
| Antibody | | HC | | LC |
| 1702 | HCDR1 | GFIF SSSA SEQ ID NO: 10 | LCDR1 | SGSVS TSHY SEQ ID NO: 13 |
| | HCDR2 | ISYD GSNK SEQ ID NO: 11 | LCDR2 | NTN SEQ ID NO: 14 |
| | HCDR3 | ARSA RLYA SFDY SEQ ID NO: 12 | LCDR3 | AIHVD RDIWV SEQ ID NO: 15 |
| 1703 | HCDR1 | GFTF SSYA SEQ ID NO: 16 | LCDR1 | QSI STY SEQ ID NO: 19 |
| | HCDR2 | ISGS GGST SEQ ID NO: 17 | LCDR2 | AYS SEQ ID NO: 20 |
| | HCDR3 | AKGV GPVH ALDV SEQ ID NO: 18 | LCDR3 | QQSYS TPMWT SEQ ID NO: 21 |

The antibody variable region was then homologously recombined with the constant region gene (CH1-FC/CL) fragment to construct the complete antibody VH-CH1-FC/VK-CL/VL-CL.

The constructed complete antibodies h1702-IgG1, h1703-IgG1 sequences are as follows:

h1702-IgG1: h1702-IgG1 heavy chain amino acid sequence: (SEQ ID NO: 22)

```
QVQLVQSGGGVVQPGTSLRLSCAASGFIFSSSAMHAWVRQAPGK
GLEWVAVISYDGSNKYYVDSVKGRFTISRDNSKNTLYLQMNSLR
AEDTAVYYCARSARLYASFDYWGQGALVTVSSASTKGPSVFPLA
PSSKSTSGGTAALGCLVKDYFPEPVTVSWNSGALTSGVHTFPAV
LQSSGLYSLSSVVTVPSSSLGTQTYICNVNHKPSNTKVDKKVEP
KSCDKTHTCPPCPAPELLGGPSVFLFPPKPKDTLMISRTPEVTC
VVVDVSHEDPEVKFNWYVDGVEVHNAKTKPREEQYNSTYRVVSV
LTVLHQDWLNGKEYKCKVSNKALAPIEKTISKAKGQPREPQVYT
LPPSRDELTKNQVSLTCLVKGFYPSDIAVEWESNGQPENNYKTT
PPVLDSDGSFFLYSKLTVDKSRWQQGNVFSCMHEALHNHYTQKS
LSLSPGK
``` h1702 light chain amino acid sequence: Lamda (SEQ ID NO: 23)

```
QTVVTQEPSFSVSPGGTVTLTCGLSSGSVSTSHYPSWYQQTPGQAPRM
LIYNTNTRSSGVPDRFSGSILGNKAALTITGAQADDESDYYCAIHVDR
DIWVFGGGTKLTVLGQPKANPTVTLFPPSSEELQANKATLVCLISDFY
PGAVTVAWKADGSPVKAGVETTKPSKQSNNKYAASSYLSLTPEQWKSH
RSYSCQVTHEGSTVEKTVAPTECS
``` h1703-IgG1: h1703-IgG1 heavy chain amino acid sequence: (SEQ ID NO: 24)

```
QVQLQESGGGLVQPGGSLRLSCAASGFTFSSYAMSWVRQAPGKGLEWVS
AISGSGGSTYYADSVKGRYTISRDNSKNTLYLQMNSLRAEDTAVYYCAK
GVGPVHALDVWGQGTTVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGFYKCKVSNKALPAPEEKT1SKAKGQP
REPQVYTLPPSRDELIKNQVSLICLVKGFYPSDIAVEWESNGQPENNYK
TTPPVLDSDGSFFLYSKLTVDKSRWQQGNVFSCSVMHEALHNHYTQKS
LSLSPGK
``` h1703 light chain amino acid sequence: Kappa (SEQ ID NO: 25)

```
DIRLTQSPSSLSASVGDRVTITCRASQSISTYLNWYQQKPGKAPILLI
NAVSGLQSGVPSRFSGSGSGTHFTLITSLQPEDFATYYCQQSYSTPMW
TFGQGTKVEIKRTVAAPSVFIFPSDEQLKSGTASVVCLLNNFNPREAK
VQWKVDNALQSGNSQESVTEQDSKDSTYSLSSTLTLSKADYEKHKVYA
CEVTHQGLSSPVTKSFNRGEC
```

In order to further improve the stability of the antibody, the amino acids of the h1702 light chain sequence were mutated, wherein the specific mutation involves that the first amino acid residue Q at N-terminus of the light chain was replaced by D, the first amino acid residue S at C-terminus was deleted, so as to obtain a more stable and uniform monoclonal antibody.

h1702-1 light chain amino acid sequence with mutation modification: (SEQ ID NO: 26)

```
DTVVTQEPSFSVSPGGTVTLTCGLSSGSVSTSHYPSWYQQTPGQAPRML
IYNTNTRSSGVPDRFSGSILGNKAALTITGAQADDESDYYCAIHVDRDI
WVFGGGTKLTVLGQPKANPTVTLFPPSSEELQANKATLVCLISDFYPGA
VTVAWKADGSPVKAGVETTKPSKQSNNKYAASSYLSLTPEQWKSHRSYS
CQVTHEGSTVEKTVAPTEC
```

Example 4

Expression and Purification of Fully Human Antibodies

The plasmids expressing the light and heavy chain of the antibody respectively were transfected into HEK293E cells at a ratio of 1.5:1. The cell culture supernatant was collected 6 days later, and the cell debris was removed by high-speed centrifugation, and purification was performed by a Protein A column. The column was washed with PBS until the A280 reading dropped to the baseline. The target protein was eluted with an acidic eluent of pH 3.0-pH 3.5 and neutralized with 1 M Tris-HCl, pH 8.0-9.0. The eluted sample was appropriately concentrated and further purified by gel chromatography Superdex 200 (GE) which was equilibrated by PBS to remove the aggregate. The monomer peak was collected and aliquoted for use.

The performance and beneficial effect of the antibodies of the present invention was tested by the following test methods:

Test Example 1

ELISA Binding Assay

To test the binding ability of the screened B7-H3 antibodies to different forms of human B7-H3 in vitro, human 2Ig-B7-H3 (Cat. #1949-B3-050/CF, R&D) and human 4Ig-B7-H3 (Cat #11188-H08H, Sino Biological) were used for binding assays in vitro.

Figure 2:
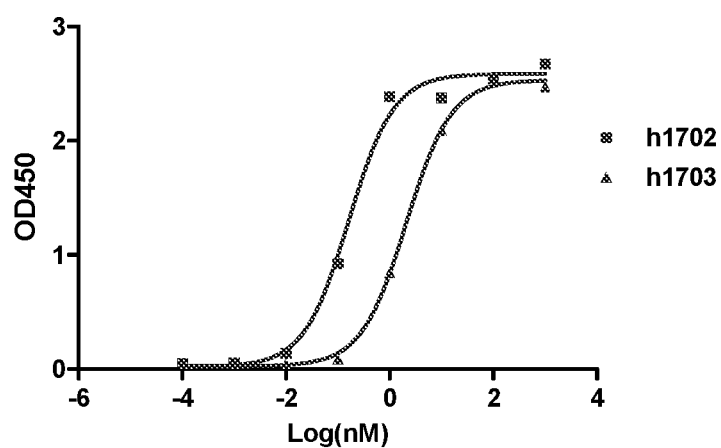
FIG. 2: Binding ability of different antibodies to human 4Ig-B7-H3 antigen.

Human B7-H3 protein (2Ig/4Ig) was diluted to a concentration of 1 μg/ml with phosphate-buffered saline (PBS) buffer, pH 7.4 (Sigma, P4417-100TAB), and added to a 96-well Elisa plate at a volume of 100 μl/well (Corning, CLS3590-100 EA), and placed at 4° C. overnight, for 16-20 hours. After discarding the liquid, 5% skim milk (Guang-Ming skim milk powder) blocking solution diluted with PBST buffer (pH 7.4 PBS containing 0.05% Tween-20) was added at 120 μl/well, and the mixture was incubated at 37° C. for 2 hours to block. At the end of the blocking, the blocking solution was discarded, and the plate was washed 4 times with PBST buffer. Then, 100 μl/well of the corresponding B7-H3 antibodies with series dilution was added. The initial concentration was 1 μM, then diluted with PBST buffer to 8 gradients, and incubated at 37° C. for 1 hour in the incubator. After incubation, the reaction solution in the plate was discarded, and the plate was washed 4 times with PBST. HRP-labeled goat anti-Human IgG Fcγ fragment specific secondary antibody (Jackson Immuno Research, 109-005-008) diluted with PBST (1:4000) was added at 100 μl/well, and incubated for 1 hour at 37° C. After washing the plate 4 times with PBST, TMB chromogenic substrate (KPL, 52-00-03) was added at 100 μl/well, incubated for 3-5 minutes (min) at room temperature, and 1 M $H_2SO_4$ was added at 100 μl/well to stop the reaction. The absorbance value was read using NOVOStar microplate reader at 450 nm, and the EC50 value for the binding between the antibody and the antigen was calculated. The results are shown in Table 2, FIG. 1 and FIG. 2.

TABLE 2

The binding ability of different antibodies to human 2Ig-B7-H3 and 4Ig-B7-H3 antigen

| EC50 | human 2Ig-B7-H3(nM) | human 4Ig-B7-H3(nM) |
|---|---|---|
| h1702 | 0.11 | 0.16 |
| h1703 | 10.28 | 2.10 |

The results show that h1702 and h1703 have significant binding ability to both human 2Ig-B7-H3 and 4Ig-B7-H3, and h1702 has stronger binding ability.

Test Example 2

Cross-Binding Assay to B7-H3 Derived From Different Species

To test the binding ability of the screened B7-H3 antibodies to B7-H3 derived from different species in vitro, murine B7-H3 (Cat. #1397-B3-050/CF, R&D) was used for binding assays in vitro.

Figure 3:
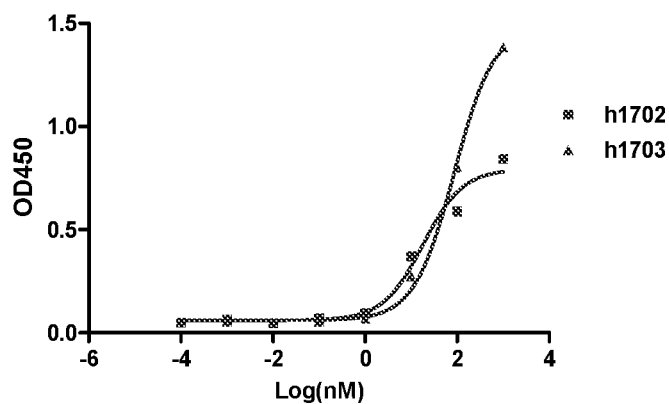
FIG. 3: Cross-binding ability of different antibodies to murine B7-H3 antigen.

B7-H3 protein derived from different species (mouse B7-H3) was diluted to a concentration of 1 μg/ml with PBS buffer, pH 7.4 (Sigma, P4417-100TAB), added to a 96-well microtiter plate at a volume of 100 μl/well (Corning, CLS3590-100 EA), and placed at 4° C. overnight for 16-20 hours. After discarding the liquid, 5% skim milk (Guang-Ming skim milk powder) blocking solution diluted with PBST buffer (pH 7.4 PBS containing 0.05% Tween-20) was added at 120 μl/well, and the mixture was incubated at 37° C. for 2 hours to block. At the end of the blocking, the blocking solution was discarded, and the plate was washed 4 times with PBST buffer. Then, 100 μl/well of the corresponding B7-H3 antibodies at an initial concentration of 1 μM were added, diluted with PBST buffer to 8 gradients, and incubated at 37° C. for 1 hour in the incubator. After incubation, the reaction solution in the plate was discarded, and the plate was washed 4 times with PBST, and HRP-labeled goat anti-Human IgG Fcγ fragment specific secondary antibody (Jackson Immuno Research, 109-005-008) diluted with PBST (1:4000) was added at 100 μl/well, incubated for 1 hour at 37° C. After washing the plate 4 times with PBST, TMB chromogenic substrate (KPL, 52-00-03) was added at 100 μl/well, incubated for 3-5 min at room temperature, and 1 M $H_2SO_4$ was added at 100 μl/well to stop the reaction, the absorbance value was read using NOVOStar microplate reader at 450 nm, the EC50 value for the binding between the antibody and the antigen was calculated (the results are shown in Table 3 and FIG. 3).

TABLE 3

The binding ability of different antibodies to murine B7-H3 antigen

| EC50 | murine B7-H3 (nM) |
|---|---|
| h1702 | 18.12 |
| h1703 | 86.68 |

The results shown that the binding ability of h1702 and h1703 to murine B7-H3 was weak, indicating that two monoclonal antibodies specifically bind to human B7-H3.

Test Example 3

Biacore Test for Antibody Affinity

The reaction affinity of anti-B7-H3 antibodies to human and murine B7-H3 was determined using a Biacore, GE instrument.

A biosensor chip Protein A (Cat. #29127556, GE) was used to affinity capture a certain amount of antibody to be tested. A series diluted of human 2Ig-B7-H3 antigen (Cat. #1949-B3-050/CF, R&D), human 4Ig-B7-H3 antigen (Cat. #11188-H08H, Sino Biological) or murine B7-H3 antigen (Cat. #1397-B3-050/CF, R&D) was flowed through the surface of the chip. Real-time reaction signal was detected by using Biacore instrument (Biacore T200, GE), in order to obtain association and dissociation curves. After completion of each cycle of dissociation, the biochip was washed and regenerated with glycine-hydrochloric acid regeneration solution (pH 1.5) (Cat. #BR-1003-54, GE). The buffer used in the experiment was HBS-EP buffer solution (pH 7.4) (Cat. #BR-1001-88, GE).

The experimental data was fitted with BIA evaluation version 4.1 GE software in a (1:1) Langmuir model to obtain affinity values. The experimental results are shown in Tables 4-6.

TABLE 4

The reaction affinity of different antibodies to human 2Ig-B7-H3 antigen

| Antibody | Antigen | Affinity (M) |
|---|---|---|
| h1702 | human 2Ig-B7-H3 | 7.97E−7 |
| h1703 |  | 4.48E−7 |

TABLE 5

The reaction affinity of different antibodies to human 4Ig-B7-H3 antigen

| Antibody | Antigen | Affinity (M) |
|---|---|---|
| h1702 | human 4Ig-B7-H3 | 8.55E−9 |
| h1703 |  | — |

TABLE 6

The reaction affinity of different antibodies to murine B7-H3 antigen

| Antibody | Antigen | Affinity (M) |
|---|---|---|
| h1702 | murine B7-H3 | 1.47E−6 |
| h1703 |  | 5.02E−7 |

The affinity results of Biacore test show that h1702 has strong affinity to human 4Ig-B7-H3, reaching a level at nM, whereas the affinity to human 2Ig-B7-H3 or murine B7-H3 is relatively weaker; h1703 has weaker affinity to human 4Ig-B7-H3, human 2Ig-B7-H3 and murine B7-H3.

Test Example 4

In Vitro Cell Binding Assay

Figure 4:
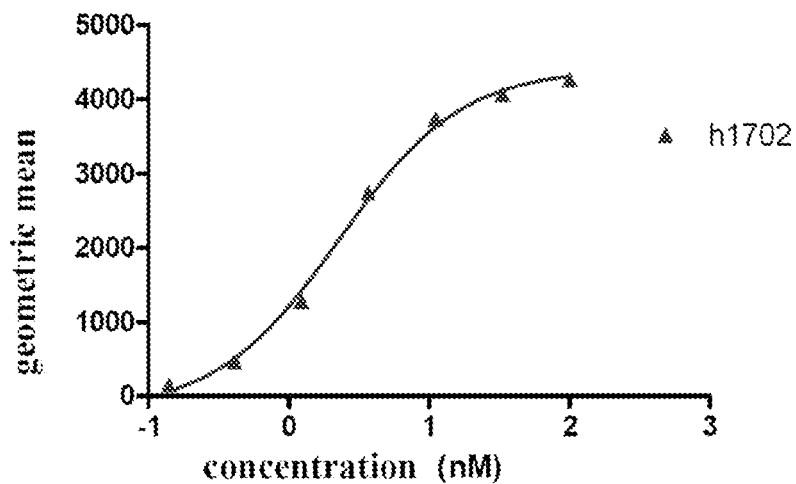
FIG. 4: Binding ability of different antibodies to U87MG cells.

In this experiment, the binding of antibody was evaluated based on the intensity of fluorescence signal of the antibody bond on the cell surface. After incubating 10 μg of primary antibody with $2 \times 10^5$ U87MG cells on ice for 30 minutes, excess antibody was removed by washing. The cells were incubated with APC anti-human IgG Fc (Biolegend, 409306) for 30 minutes at room temperature, and after removing excess antibody, the fluorescence signal on the cell surface was read using BD Verse (results were shown in FIG. 4). The results indicate that h1702 specifically binds to U87MG tumor cells which overexpress B7-H3.

Test Example 5

In Vitro Endocytosis Test

Figure 5:
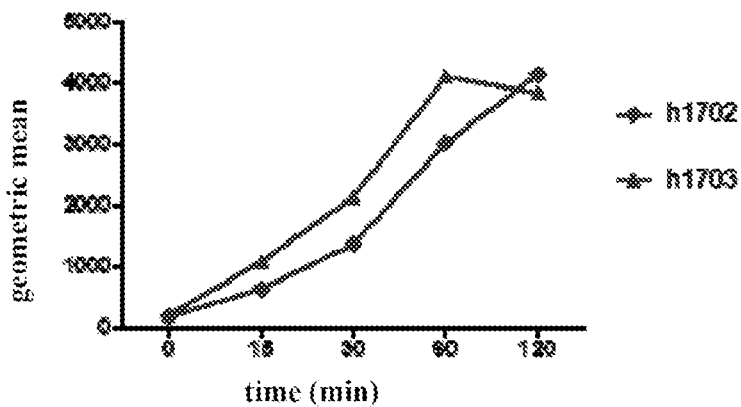
FIG. 5: Endocytic effect of different antibodies on U87MG cells.

In this experiment, the endocytosis effect of the antibody was evaluated based on the intensity of fluorescence signal which was determined of the internalized antibody. The B7-H3 antibody and APC anti-human IgG Fc (Biolegend, 409306) were mixed at a molar ratio of 1:2 and incubated on ice for 15 minutes. After incubating the antibody mixture with $2 \times 10^5$ U87MG cells on ice for 30 minutes, excess antibody was removed by washing, and then the cells were transferred to a 37° C. prewarmed medium, and incubated at 37° C. for 0, 15, 30, 60 and 120 minutes respectively. The cells were centrifuged and resuspended in the antibody elution buffer to get rid of antibodies. After incubating for 7 minutes at room temperature, the antibody elution buffer was removed by washing, and the intracellular fluorescence signal was read using BD Verse (results shown in FIG. 5). The results show that both h1702 and h1703 were efficiently endocytosed into cells after binding to U87MG cells.

Test Example 6

T1/2 Evaluation on SD Rats

4 SD rats (purchased from JSJ Experimental Animal Co., Ltd.), 2 males and 2 females, were maintained in light/dark cycle adjusted at 12/12 hours, with constant temperature of 24±3° C., humidity of 50-60%, and free access to food and water. On the day of the experiment, SD rats were injected with the test agent into tail vein at a dose of 3 mg/kg and an injection volume of 5 ml/kg.

The time for blood collection: On the first day of administration, blood was taken from ocular fundus vein at 5 min, 8 h, 24 h, 2 days, 3 days, 5 days, 8 days, and 15 days after administration, 200 μL each time (equivalent to 100 μL of serum). The collected blood samples were allowed to incubateat room temperature for half an hour until coagulation, and then centrifuged at 10,000×g for 10 minutes at 4° C. The supernatant was collected and immediately stored at −80° C. The B7-H3 antibody concentration in the serum was measured by ELISA, and PK analysis was performed. The results are shown in Table 7.

TABLE 7

$T_{1/2}$ of B7-H3 antibody in SD rats

| Tested agent | Route of administration | $T_{1/2}$ (mean ± SD, h) |
|---|---|---|
| h1702 | IV (3 mg/kg) | 185 ± 17 |

The results show that the half-life of the antibody of the present invention in rats was approximately 185 h (7.7 days).

Test Example 7

Physical Stability of B7-H3 Antibodies

Differential scanning calorimetry (DSC) was used to detect the thermal stability of different antibodies, and the thermal stability in different buffer systems under different pH conditions was compared. Exemplary buffer systems corresponding to different pHs were 10 mM PB (pH 7) and 10 mM Acetate (pH 5.2). The sample was dissolved in the corresponding buffer, and the sample concentration was controlled at about 1 mg/ml. Detection was performed using MicroCal* VP-Capillary DSC (Malvern). Before detection, each sample and the blank buffer were degassed by a vacuum degasser for 1 to 2 minutes. 400 μl of sample or blank buffer were added to each well of the sample plate (the load of instrument is 300 μl). The last two pairs of wellplates were respectively added with 14% Decon 90 and ddH$_2$O for cleaning. After the sample plate was loaded, a plastic soft cover was placed. The scanning temperature started from 25° C. and ended at 100° C. The scanning rate was 60° C./h. The results are shown in Table 8. In several test systems, both h1702 and h1703 showed good thermal stability.

TABLE 8

DSC results of different antibodies

| Sample | Buffer | Tm-onset (° C.) | TM (° C.) |
|---|---|---|---|
| h1702 | pH 7.0 | 65.82 | 77.51 |
|  | pH 5.2 | 65.59 | 78.97 |
| h1703 | pH 7.0 | 61.33 | 73.19 |
|  | pH 5.2 | 60.65 | 75.71 |

The purity of the sample was monitored by SEC-HPLC to investigate the stability under a certain concentration condition. As an example of condition, the sample concentration was controlled at about 40-50 mg/ml. The stability of different antibodies was compared in PBS (pH 7.4) system and pH 5.2 acetic acid/sucrose system at 4° C., 30° C., 40° C. for one month of storage. The purity of the antibody was examined using Xbridge protein BEH SEC 200A (Waters) HPLC column. After one month of investigation, both h1702 and h1703 showed good stability. The results are shown in Table 9.

TABLE 9

Stability results for different antibodies

| Sample | 4° C./month/ purity | 30° C./month/ purity | 40° C./month/ purity |
|---|---|---|---|
| h1702/acetic acid | 99.25% | 98.68% | 97.85% |
| h1702/PBS | 99.21% | 98.07% | 96.34% |
| h1703/acetic acid | 99.31% | 99.04% | 98.38% |
| h1703/PBS | 99.18% | 98.56% | 96.99% |

The results show that both h1702 and h1703 show excellent stability in both acetic acid and PBS buffers.

Test Example 8

Chemical Stability of B7-H3 Antibodies

Chemical modification after antibody preparation is one of the common reasons leading to the product stability problem, especially the high degree of deamination, oxidation or isomerization modification at some amino acids in the CDR region. Those modifications should be avoided or reduced. 500 μg of the antibodies to be tested was dissolved in 500 μl of PBS pH 7.4, and subjected to a water bath at 40° C. Samples were taken at day 0, 10, and 20, respectively, for enzymatic hydrolysis experiments. 100 μg samples were taken at different time points and dissolved in 100 μl solution of 0.2 M His-HCl, 8 M Gua-HCl, pH 6.0; 3 μl of 0.1 g/mL DTT was added, and subjected to water bath at 50° C. for 1 hour; Afterward, the samples were ultra-filtered twice with solution of 0.02 M His-HCl, pH 6.0, and 3 μL of 0.25 mg/mL trypsin was added. The mixture was hydrolyzed overnight at 37° C. in water bath. Potential modification sites were analyzed by mass spectrometry (the results are shown in Table 10) using Agilent 6530 Q-TOF. The results show that h1702 and h1703 described in the present invention have no significantly increased trend towards deamidation, oxidation or heterogeneity, indicating that the molecules have excellent chemical stability.

TABLE 10

Chemical stability of different antibodies

| Sample | LC/HC | position/modification | D 0 | D 10 | D 20 |
|---|---|---|---|---|---|
| h1702 | LC | M48/oxidation | 2.82% | 2.9% | 2.83% |
| | HC | M34/oxidation | 3.52% | 3.46% | 3.38% |
| | | M83/oxidation | 0.98% | 1.01% | 0.01% |
| h1703 | HC | M34/oxidation | 1.93% | 2.62% | 2.16% |
| | | M83/oxidation | 1.96% | 2.62% | 2.8% |

Test Example 9

Stability of h1702-1 Antibody

The lambda type light chain has one more amino acid S at the C-terminus than kappa type light chain, and the steric hindrance of the S may be a factor causing instability of interchain disulfide bond between light and heavy chain. The terminal amino acid S can be knocked out by molecular cloning, and the stability of the antibody under alkaline condition would be remarkably improved.

When the first amino acid at the N-terminus of the light chain of the naked antibody is Q, partial cyclization would also occur in the antibody, which leads to an increase in charge heterogeneity of the sample, affecting the stability of formulation and product. The first amino acid Q at N-terminus was mutated to D by molecular cloning, to eliminate the incomplete cyclization and significantly improve the antibody stability. The above modification did not significantly affect the affinity of the engineered antibody to its antigen.

The stability of h1702 and h1702-1 was tested by size-exclusion chromatography (SEC), non-reducing CE-SDS analysis method (pH 9.0) and IEX analysis method.

SEC detection: Waters e2695 chromatograph and Xbridge BEH 200A SEC column were used. 50 μg of antibody was loaded, and the elution was performed using PBS mobile phase in constant gradient.

CE-SDS NR Method

Samples were processed using the Beckman SDS-MW Analysis Kit. A buffer solution was added to 100 μg tested antibody was denatured by heating in sample buffer as described in manned protocol. Data was collected using PA800 capillary electrophoresis apparatus.

IEX Method

Waters Acquity H-Class chromatograph and Thermo MAbPac SCX-10 column were used. 50 μg of tested antibody was loaded, and a linear gradient was applied, using CX-1 pH Gradient Buffer Kit as the mobile phase; ultraviolet signal at a wavelength of 280 nm was collected.

TABLE 11

Comparison of stability of h1702 and h1702-1

| | SEC | CE-SDS (pH 9.0) | IEX |
|---|---|---|---|
| h1702 | 100% | 71.21% | 40.5% |
| h1702-1 | 100% | 94.67% | 86.21% |

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

It is claimed:

1. A method for treating a cancer related to a B7-H3 positive cancer cell, wherein the method comprises administering to a subject in need thereof a pharmaceutical composition comprising a therapeutically effective amount of a monoclonal anti-B7-H3 antibody or antigen-binding fragment thereof comprising:
  (i) an antibody heavy chain variable region comprising HCDR1, HCDR2, and HCDR3 having the amino acid sequences of SEQ ID NOs: 10, 11 and 12, respectively; and an antibody light chain variable region comprising LCDR1, LCDR2, and LCDR3 having the amino acid sequences of SEQ ID NOs: 13, 14 and 15, respectively; or
  (ii) an antibody heavy chain variable region comprising HCDR1, HCDR2, and HCDR3 having the amino acid sequences of SEQ ID NOs: 16, 17 and 18, respectively; and an antibody light chain variable region comprising LCDR1, LCDR2, and LCDR3 having the amino acid sequences of SEQ ID NOs: 19, 20 and 21, respectively.

2. The method according to claim 1, wherein the monoclonal antibody or antigen-binding fragment thereof is a recombinant antibody.

3. The method according to claim 1, wherein the monoclonal antibody or antigen-binding fragment thereof is a human recombinant antibody or antigen-binding fragment thereof.

4. The method according to claim 3, wherein the human recombinant antibody or antigen-binding fragment thereof comprises a human germline light chain framework (FR) sequence or a modified human germline light chain FR sequence, and a human germline heavy chain FR sequence or a modified human germline heavy chain FR sequence.

5. The method according to claim 4, wherein the human recombinant antibody or antigen-binding fragment thereof comprises a heavy chain variable region having the amino acid sequence of SEQ ID NO: 6 or 8 or a variant thereof; wherein the variant has a deletion, substitution or addition of 1-10 amino acids in the heavy chain variable region of SEQ ID NO: 6 or 8.

6. The method according to claim 4, wherein the human recombinant antibody or antigen-binding fragment thereof comprises a light chain variable region having the amino acid sequence of SEQ ID NO: 7 or 9 or a variant thereof; wherein the variant has a deletion, substitution or addition of 1-10 amino acids in the light chain variable region of SEQ ID NO: 7 or 9.

7. The method according to claim 1, wherein the anti-B7-H3 antibody or antigen-binding fragment thereof further comprises a human antibody constant region, and the anti-B7-H3 antibody is a full-length antibody having the heavy chain and light chain amino acid sequences as shown in SEQ ID NOs: 22 and 23, respectively, or a full-length antibody having the heavy chain and light chain amino acid sequences as shown in SEQ ID NOs: 22 and 26, respectively, or a full-length antibody having the heavy chain and light chain amino acid sequences as shown in SEQ ID NOs: 24 and 25, respectively.

8. The method according to claim 1, wherein the antigen-binding fragment is selected from the group consisting of a Fab, Fab', F(ab')2 and single-chain antibody (scFv), dimerized V region (diabody), disulfide-stabilized V region (dsFv) and CDR-containing peptide.

9. A method for treating a cancer related to a B7-H3 positive cancer cell, wherein the method comprises administering to a subject in need thereof a pharmaceutical composition comprising a therapeutically effective amount of a monoclonal anti-B7-H3 antibody or antigen-binding fragment thereof comprising an antibody heavy chain variable region comprising HCDR1, HCDR2, and HCDR3 having the amino acid sequences of SEQ ID NOs: 10, 11 and 12, respectively; and an antibody light chain variable region comprising LCDR1, LCDR2, and LCDR3 having the amino acid sequences of SEQ ID NOs: 13, 14 and 15, respectively.

10. The method according to claim 9, wherein the monoclonal antibody or antigen-binding fragment thereof comprises a heavy chain variable region having the amino acid sequence of SEQ ID NO: 6 and a light chain variable region having the amino acid sequence of SEQ ID NO: 7.

11. The method according to claim 9, wherein the monoclonal antibody or antigen-binding fragment thereof comprises a heavy chain having the amino acid sequence of SEQ ID NO: 22 and a light chain having the amino acid sequence of SEQ ID NO: 23 or 26.

12. A method for treating a cancer related to a B7-H3 positive cancer cell, wherein the method comprises administering to a subject in need thereof a pharmaceutical composition comprising a therapeutically effective amount of a monoclonal anti-B7-H3 antibody or antigen-binding fragment thereof comprising an antibody heavy chain variable region comprising HCDR1, HCDR2, and HCDR3 having the amino acid sequences of SEQ ID NOs: 16, 17 and 18, respectively; and an antibody light chain variable region comprising LCDR1, LCDR2, and LCDR3 having the amino acid sequences of SEQ ID NOs: 19, 20 and 21, respectively.

13. The method according to claim 12, wherein the human recombinant antibody or antigen-binding fragment thereof comprises a heavy chain variable region having the amino acid sequence of SEQ ID NO: 8 and a light chain variable region having the amino acid sequence of SEQ ID NO: 9.

14. The method according to claim 12, wherein the monoclonal antibody comprises a heavy chain having the amino acid sequence of SEQ ID NO: 24 and a light chain having the amino acid sequence of SEQ ID NO: 25.

15. The method of claim 1, wherein said cancer is selected from the group comprising lung cancer, renal cancer, urinary tract epithelial cancer, colorectal cancer, prostate cancer, pancreatic cancer, glioblastoma, adenocarcinoma, esophageal carcinoma, cervical cancer, osteosarcoma and neuroblastoma.

16. The method of claim 9, wherein said cancer is selected from the group comprising lung cancer, renal cancer, urinary tract epithelial cancer, colorectal cancer, prostate cancer, pancreatic cancer, glioblastoma, adenocarcinoma, esophageal carcinoma, cervical cancer, osteosarcoma and neuroblastoma.

17. The method of claim 12, wherein said cancer is selected from the group comprising lung cancer, renal cancer, urinary tract epithelial cancer, colorectal cancer, prostate cancer, pancreatic cancer, glioblastoma, adenocarcinoma, esophageal carcinoma, cervical cancer, osteosarcoma and neuroblastoma.

* * * * *

SEQUENCE LISTING

<160> NUMBER OF SEQ ID NOS: 26

<210> SEQ ID NO 1
<211> LENGTH: 534
<212> TYPE: PRT
<213> ORGANISM: Homo sapiens
<220> FEATURE:
<221> NAME/KEY: PEPTIDE
<223> OTHER INFORMATION: Human B7H3 full-length amino acid sequence

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

-continued

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
            515                 520                 525

Asp Gly Gln Glu Ile Ala
            530

<210> SEQ ID NO 2
<211> LENGTH: 316
<212> TYPE: PRT
<213> ORGANISM: Mus musculus
<220> FEATURE:
<221> NAME/KEY: PEPTIDE
<223> OTHER INFORMATION: Murine B7H3 full-length amino acid sequence

<400> SEQUENCE: 2

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
            20                  25                  30

Val Ser Glu Asp Pro Val Val Ala Leu Val Asp Thr Asp Ala Thr Leu
            35                  40                  45

Arg Cys Ser Phe Ser Pro Glu Pro Gly Phe Ser Leu Ala Gln Leu Asn
50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
            85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
            115                 120                 125

Phe Asp Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
            165                 170                 175

Phe Trp Lys Asp Gly Gln Gly Val Pro Leu Thr Gly Asn Val Thr Thr
            180                 185                 190

Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser
                245                 250                 255

Val Cys Leu Val Val Leu Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Asp Gly Glu Gly Ser Lys Thr Ala Leu Arg Pro Leu Lys Pro
290                 295                 300

Ser Glu Asn Lys Glu Asp Gly Gln Glu Ile Ala
305                 310                 315

<210> SEQ ID NO 3
<211> LENGTH: 223
<212> TYPE: PRT
<213> ORGANISM: Artificial Sequence
<220> FEATURE:
<221> NAME/KEY: PEPTIDE
<223> OTHER INFORMATION: Human B7H3 antigen: 2Ig-B7H3

<400> SEQUENCE: 3

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly His His His His His His

-continued

```
            210                 215                 220
```

<210> SEQ ID NO 4
<211> LENGTH: 439
<212> TYPE: PRT
<213> ORGANISM: Artificial Sequence
<220> FEATURE:
<221> NAME/KEY: PEPTIDE
<223> OTHER INFORMATION: Human B7H3 antigen: 4Ig-B7H3

<400> SEQUENCE: 4

```
Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350
```

```
Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
                420                 425                 430

Thr His His His His His His
        435
```

```
<210> SEQ ID NO 5
<211> LENGTH: 222
<212> TYPE: PRT
<213> ORGANISM: Artificial Sequence
<220> FEATURE:
<221> NAME/KEY: PEPTIDE
<223> OTHER INFORMATION: Murine B7H3 antigen

<400> SEQUENCE: 5

Val Glu Val Gln Val Ser Glu Asp Pro Val Val Ala Leu Val Asp Thr
1               5                   10                  15

Asp Ala Thr Leu Arg Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
                35                  40                  45

His Ser Phe Thr Glu Gly Arg Asp Gln Gly Ser Ala Tyr Ser Asn Arg
    50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Phe Val
                85                  90                  95

Ser Ile Gln Asp Phe Asp Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asn Met Val Thr Ile Thr Cys Ser Ser Tyr Gln Gly Tyr Pro
    130                 135                 140

Glu Ala Glu Val Phe Trp Lys Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
            195                 200                 205

Ile Thr Gly Gln Pro Leu Thr Phe His His His His His His
    210                 215                 220
```

```
<210> SEQ ID NO 6
<211> LENGTH: 119
<212> TYPE: PRT
<213> ORGANISM: Artificial Sequence
<220> FEATURE:
<221> NAME/KEY: DOMAIN
<223> OTHER INFORMATION: h1702 Heavy chain variable region
```

<400> SEQUENCE: 6

Gln Val Gln Leu Val Gln Ser Gly Gly Val Val Gln Pro Gly Thr
1               5                   10                  15

Ser Leu Arg Leu Ser Cys Ala Ala Ser Gly Phe Ile Phe Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser
        115

<210> SEQ ID NO 7
<211> LENGTH: 110
<212> TYPE: PRT
<213> ORGANISM: Artificial Sequence
<220> FEATURE:
<221> NAME/KEY: DOMAIN
<223> OTHER INFORMATION: h1702 light chain variable region

<400> SEQUENCE: 7

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu
            100                 105                 110

<210> SEQ ID NO 8
<211> LENGTH: 119
<212> TYPE: PRT
<213> ORGANISM: Artificial Sequence
<220> FEATURE:
<221> NAME/KEY: DOMAIN
<223> OTHER INFORMATION: h1703 Heavy chain variable region

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Tyr Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Val Gly Pro Val His Ala Leu Asp Val Trp Gly Gln Gly
            100                 105                 110

Thr Thr Val Thr Val Ser Ser
        115

<210> SEQ ID NO 9
<211> LENGTH: 108
<212> TYPE: PRT
<213> ORGANISM: Artificial Sequence
<220> FEATURE:
<221> NAME/KEY: DOMAIN
<223> OTHER INFORMATION: h1703 light chain variable region

<400> SEQUENCE: 9

Asp Ile Arg Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Ile Leu Leu Ile
        35                  40                  45

Asn Ala Val Ser Gly Leu Gln Ser Gly Val Pro Ser Arg Phe Ser Gly
    50                  55                  60

Ser Gly Ser Gly Thr His Phe Thr Leu Thr Ile Thr Ser Leu Gln Pro
 65                  70                  75                  80

Glu Asp Phe Ala Thr Tyr Tyr Cys Gln Gln Ser Tyr Ser Thr Pro Met
                 85                  90                  95

Trp Thr Phe Gly Gln Gly Thr Lys Val Glu Ile Lys
            100                 105

<210> SEQ ID NO 10
<211> LENGTH: 8
<212> TYPE: PRT
<213> ORGANISM: Artificial Sequence
<220> FEATURE:
<221> NAME/KEY: DOMAIN
<223> OTHER INFORMATION: h1702 HCDR1

<400> SEQUENCE: 10

Gly Phe Ile Phe Ser Ser Ser Ala
 1               5

<210> SEQ ID NO 11
<211> LENGTH: 8
<212> TYPE: PRT
<213> ORGANISM: Artificial Sequence
<220> FEATURE:
<221> NAME/KEY: DOMAIN
<223> OTHER INFORMATION: h1702 HCDR2

<400> SEQUENCE: 11

Ile Ser Tyr Asp Gly Ser Asn Lys
 1               5

<210> SEQ ID NO 12
<211> LENGTH: 12
<212> TYPE: PRT

```
<213> ORGANISM: Artificial Sequence
<220> FEATURE:
<221> NAME/KEY: DOMAIN
<223> OTHER INFORMATION: h1702 HCDR3

<400> SEQUENCE: 12

Ala Arg Ser Ala Arg Leu Tyr Ala Ser Phe Asp Tyr
1               5                   10

<210> SEQ ID NO 13
<211> LENGTH: 9
<212> TYPE: PRT
<213> ORGANISM: Artificial Sequence
<220> FEATURE:
<221> NAME/KEY: DOMAIN
<223> OTHER INFORMATION: h1702 LCDR1

<400> SEQUENCE: 13

Ser Gly Ser Val Ser Thr Ser His Tyr
1               5

<210> SEQ ID NO 14
<211> LENGTH: 3
<212> TYPE: PRT
<213> ORGANISM: Artificial Sequence
<220> FEATURE:
<221> NAME/KEY: DOMAIN
<223> OTHER INFORMATION: h1702 LCDR2

<400> SEQUENCE: 14

Asn Thr Asn
1

<210> SEQ ID NO 15
<211> LENGTH: 10
<212> TYPE: PRT
<213> ORGANISM: Artificial Sequence
<220> FEATURE:
<223> OTHER INFORMATION: h1702 LCDR3

<400> SEQUENCE: 15

Ala Ile His Val Asp Arg Asp Ile Trp Val
1               5                   10

<210> SEQ ID NO 16
<211> LENGTH: 8
<212> TYPE: PRT
<213> ORGANISM: Artificial Sequence
<220> FEATURE:
<221> NAME/KEY: DOMAIN
<223> OTHER INFORMATION: h1703 HCDR1

<400> SEQUENCE: 16

Gly Phe Thr Phe Ser Ser Tyr Ala
1               5

<210> SEQ ID NO 17
<211> LENGTH: 8
<212> TYPE: PRT
<213> ORGANISM: Artificial Sequence
<220> FEATURE:
<221> NAME/KEY: DOMAIN
<223> OTHER INFORMATION: h1703 HCDR2

<400> SEQUENCE: 17

Ile Ser Gly Ser Gly Gly Ser Thr
1               5
```

<210> SEQ ID NO 18
<211> LENGTH: 12
<212> TYPE: PRT
<213> ORGANISM: Artificial Sequence
<220> FEATURE:
<221> NAME/KEY: DOMAIN
<223> OTHER INFORMATION: h1703 HCDR3

<400> SEQUENCE: 18

Ala Lys Gly Val Gly Pro Val His Ala Leu Asp Val
1               5                   10

<210> SEQ ID NO 19
<211> LENGTH: 6
<212> TYPE: PRT
<213> ORGANISM: Artificial Sequence
<220> FEATURE:
<221> NAME/KEY: DOMAIN
<223> OTHER INFORMATION: h1703 LCDR1

<400> SEQUENCE: 19

Gln Ser Ile Ser Thr Tyr
1               5

<210> SEQ ID NO 20
<211> LENGTH: 3
<212> TYPE: PRT
<213> ORGANISM: Artificial Sequence
<220> FEATURE:
<221> NAME/KEY: DOMAIN
<223> OTHER INFORMATION: h1703 LCDR2

<400> SEQUENCE: 20

Ala Val Ser
1

<210> SEQ ID NO 21
<211> LENGTH: 10
<212> TYPE: PRT
<213> ORGANISM: Artificial Sequence
<220> FEATURE:
<221> NAME/KEY: DOMAIN
<223> OTHER INFORMATION: h1703 LCDR3

<400> SEQUENCE: 21

Gln Gln Ser Tyr Ser Thr Pro Met Trp Thr
1               5                   10

<210> SEQ ID NO 22
<211> LENGTH: 449
<212> TYPE: PRT
<213> ORGANISM: Artificial Sequence
<220> FEATURE:
<221> NAME/KEY: DOMAIN
<223> OTHER INFORMATION: h1702-IgG1 heavy chain

<400> SEQUENCE: 22

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ala Arg Leu Tyr Ala Ser Phe Asp Tyr Trp Gly Gln Gly
            100                 105                 110

Ala Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 23
<211> LENGTH: 216
<212> TYPE: PRT
<213> ORGANISM: Artificial Sequence
```

-continued

```
<220> FEATURE:
<221> NAME/KEY: DOMAIN
<223> OTHER INFORMATION: h1702 light chain

<400> SEQUENCE: 23
```

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

```
<210> SEQ ID NO 24
<211> LENGTH: 449
<212> TYPE: PRT
<213> ORGANISM: Artificial Sequence
<220> FEATURE:
<221> NAME/KEY: DOMAIN
<223> OTHER INFORMATION: h1703-IgG1 heavy chain

<400> SEQUENCE: 24
```

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Tyr Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Gly Pro Val His Ala Leu Asp Val Trp Gly Gln Gly
            100                 105                 110

```
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 25
<211> LENGTH: 215
<212> TYPE: PRT
<213> ORGANISM: Artificial Sequence
<220> FEATURE:
<221> NAME/KEY: DOMAIN
<223> OTHER INFORMATION: h1703 light chain

<400> SEQUENCE: 25

Asp Ile Arg Leu Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Ile Leu Leu Ile
        35                  40                  45

Asn Ala Val Ser Gly Leu Gln Ser Gly Val Pro Ser Arg Phe Ser Gly
    50                  55                  60

Ser Gly Ser Gly Thr His Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Met
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 26
<211> LENGTH: 215
<212> TYPE: PRT
<213> ORGANISM: Artificial Sequence
<220> FEATURE:
<221> NAME/KEY: DOMAIN
<223> OTHER INFORMATION: h1702-1 light chain

<400> SEQUENCE: 26

Asp Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
```

```
                  145                 150                 155                 160
Ala Gly Val Glu Thr Thr Lys Pro Ser Lys Gln Ser Asn Asn Lys Tyr
                    165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys
        210                 215
```